(12) United States Patent
Moore

(10) Patent No.: US 11,511,094 B2
(45) Date of Patent: Nov. 29, 2022

(54) APPARATUS AND METHOD FOR DEPLOYING A SURGICAL PREPARATION

(71) Applicant: Mark R. Moore, Westlake, LA (US)

(72) Inventor: Mark R. Moore, Westlake, LA (US)

(*) Notice: Subject to any disclaimer, the term of this patent is extended or adjusted under 35 U.S.C. 154(b) by 906 days.

(21) Appl. No.: 16/280,914

(22) Filed: Feb. 20, 2019

(65) Prior Publication Data
US 2019/0184146 A1    Jun. 20, 2019

Related U.S. Application Data

(63) Continuation-in-part of application No. 15/459,690, filed on Mar. 15, 2017, now Pat. No. 10,470,842,
(Continued)

(51) Int. Cl.
A61M 35/00 (2006.01)
A61B 90/80 (2016.01)
(Continued)

(52) U.S. Cl.
CPC ............ A61M 35/00 (2013.01); A61B 90/80 (2016.02); A61H 7/002 (2013.01); A61H 9/0092 (2013.01); A61H 33/6005 (2013.01); A61H 33/6068 (2013.01); A61H 35/006 (2013.01); A61B 90/40 (2016.02); A61H 2201/0103 (2013.01);
(Continued)

(58) Field of Classification Search
CPC ........ A61F 13/06; A61F 13/10; A61F 15/004; A61F 15/006; A61F 15/008; A61H 33/00; A61H 33/6005; A61H 33/6068; A61H 35/00; A61H 35/006; A61M 35/00; A61B 90/40; A61B 90/80
See application file for complete search history.

(56) References Cited

U.S. PATENT DOCUMENTS 871,689 A    11/1907  Ganzhorn
2,690,747 A  10/1954  Frallic
(Continued)

FOREIGN PATENT DOCUMENTS

WO    2017216050    12/2017

OTHER PUBLICATIONS

Negosanti, Luca, Valentina Pinto, and Rossella Sgarzani. "Clinical evidences, personal experiences, recent applications." World Journal of Dermatology 1.3 (2012): 13-23.
(Continued)

Primary Examiner — Catharine L Anderson
(74) Attorney, Agent, or Firm — Schultz & Associates, P.C.

(57) ABSTRACT

A device used for applying an antiseptic preparation, such as an antibiotic solution or water, or all other substance deemed necessary in treating a wound prior to arrival at a hospital or other treatment facility or for continuing wound therapy and maintenance while hospitalized, in an out-patient facility or at home. A loose-fitting bag is provided which encloses the wound by securing the open end(s) to the patient by closing means. The bag further includes ports or resealable flaps that allow access to the wound for treatment and cleaning while containing all fluids resulting therefrom. A high friction scrub surface is provided in the bag. A method and apparatus are also provided for wound maintenance with a lavage system.

8 Claims, 31 Drawing Sheets

Related U.S. Application Data which is a continuation-in-part of application No. 15/005,750, filed on Jan. 25, 2016, now Pat. No. 10,188,842, which is a continuation-in-part of application No. 14/312,498, filed on Jun. 23, 2014, now Pat. No. 9,409,005, which is a continuation-in-part of application No. 13/199,343, filed on Aug. 26, 2011, now Pat. No. 8,758,310, which is a continuation-in-part of application No. 11/602,542, filed on Nov. 21, 2006, now Pat. No. 8,403,898.

(51) Int. Cl.
*A61H 33/00* (2006.01)
*A61H 35/00* (2006.01)
*A61H 7/00* (2006.01)
*A61H 9/00* (2006.01)
*A61B 90/40* (2016.01)

(52) U.S. Cl.
CPC ............ *A61H 2201/1207* (2013.01); *A61H 2201/1623* (2013.01); *A61H 2201/1638* (2013.01); *A61H 2201/1642* (2013.01); *A61H 2201/1654* (2013.01); *A61H 2205/06* (2013.01); *A61H 2205/065* (2013.01); *A61H 2205/081* (2013.01); *A61H 2205/083* (2013.01); *A61H 2205/088* (2013.01); *A61H 2205/10* (2013.01); *A61H 2205/12* (2013.01)

(56) References Cited

U.S. PATENT DOCUMENTS

| | | |
|---|---|---|
| 3,327,705 A | 6/1967 | Spira et al. |
| 3,744,491 A | 7/1973 | Fischer |
| 4,376,437 A | 3/1983 | Sundheim et al. |
| 4,691,695 A | 9/1987 | Birk et al. |
| 4,772,259 A | 9/1988 | Frech et al. |
| 4,808,172 A | 2/1989 | Murata |
| 4,858,604 A | 8/1989 | Konishi |
| 5,029,579 A | 7/1991 | Trammell |
| 5,312,385 A | 5/1994 | Greco |
| 5,447,504 A | 9/1995 | Baker |
| 5,592,953 A | 1/1997 | Delao |
| 5,609,163 A | 3/1997 | Beard |
| 5,702,356 A | 12/1997 | Hathman |
| 5,769,806 A | 6/1998 | Radow |
| 5,823,977 A | 10/1998 | Dalyea |
| 5,848,998 A | 12/1998 | Marasco |
| 5,865,722 A | 2/1999 | Heng |
| 6,007,564 A | 12/1999 | Haverstock |
| 6,083,209 A | 7/2000 | Marasco |
| 6,241,697 B1 | 6/2001 | Augustine |
| 6,450,982 B1 | 9/2002 | Peterson |
| 6,562,013 B1 | 5/2003 | Marasco |
| 6,620,379 B1 | 9/2003 | Piuk et al. |
| 6,635,035 B1 | 10/2003 | Marasco |
| 6,664,434 B2 | 12/2003 | Cominsky |
| 6,992,233 B2 | 1/2006 | Drake et al. |
| 7,771,402 B2 | 8/2010 | Marasco |
| 8,048,044 B2 | 11/2011 | Stryker |
| 8,100,887 B2 | 1/2012 | Weston et al. |
| 8,158,844 B2 | 4/2012 | McNeil |
| 8,182,521 B2 | 5/2012 | Kane et al. |
| 8,206,363 B2 | 6/2012 | Bainbridge |
| 8,298,197 B2 | 10/2012 | Eriksson |
| 8,353,882 B1 | 1/2013 | Pelkus |
| 8,403,898 B2 | 3/2013 | Moore |
| 8,568,375 B2 | 10/2013 | Marasco |
| 8,603,150 B2 | 12/2013 | Kane et al. |
| 8,657,796 B2 | 2/2014 | Marasco |
| 8,679,050 B2 | 3/2014 | Nakamura |
| 8,708,998 B2 | 4/2014 | Weston et al. |
| 9,017,278 B2 | 4/2015 | Nakamura |
| 9,101,526 B2 | 8/2015 | Nakamura |
| 9,211,227 B2 | 12/2015 | Loori et al. |
| 9,579,431 B2 | 2/2017 | Buan et al. |
| 9,693,908 B2 | 7/2017 | Eriksson et al. |
| 10,004,884 B2 | 6/2018 | Allan et al. |
| 2004/0171998 A1 | 9/2004 | Marasco |
| 2005/0043672 A1 | 2/2005 | Piuk et al. |
| 2011/0040239 A1 | 2/2011 | Schnieder et al. |
| 2011/0130712 A1 | 6/2011 | Topaz |
| 2011/0288458 A1 | 11/2011 | Jones et al. |
| 2012/0246820 A1 | 10/2012 | Huynh |
| 2014/0316455 A1* | 10/2014 | Gnanashanmugam ..................... A61G 13/108 606/1 |
| 2014/0343517 A1 | 11/2014 | Jameson |
| 2015/0119772 A1 | 4/2015 | Ruetenik |
| 2015/0119823 A1 | 4/2015 | Marasco |
| 2017/0007460 A1 | 1/2017 | Macdonald et al. |

OTHER PUBLICATIONS

Zhao, Jing-Chun, et al. "Hypertonic Glucose Combined with Negative Pressure Wound Therapy to Prepare Wounds with Pseudomonas aeruginosa Infection for Skin Grafting: A Report of 3 Cases." Ostomy/wound management 61.6 (2015): 28-44.

Amouzou, Komla S., et al. "Use of domestic negative pressure wound therapy in traumatic wounds for a cost-effective wound closure." Nigerian Journal of Plastic Surgery 13.2 (2017): 64.

\* cited by examiner

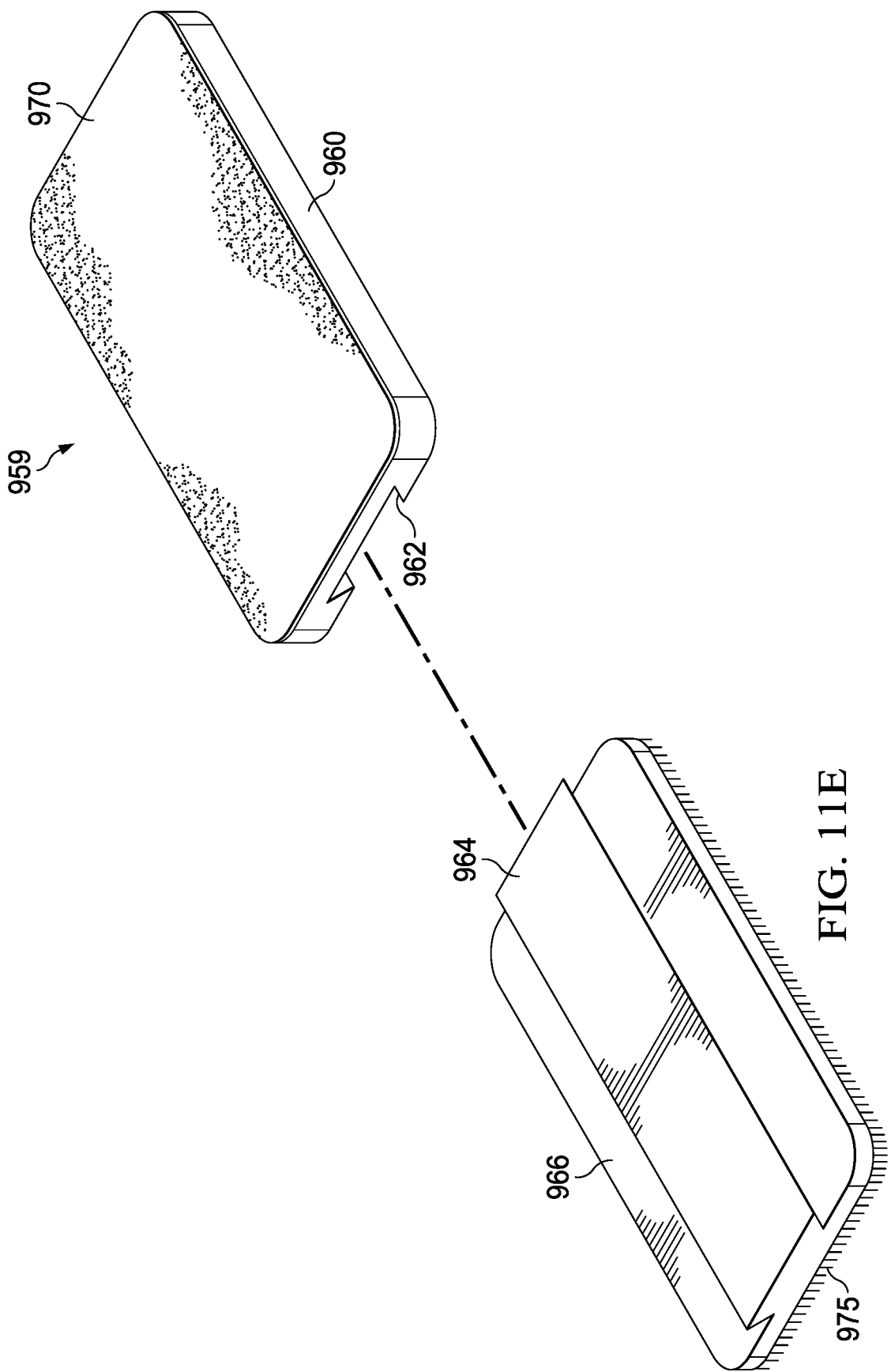

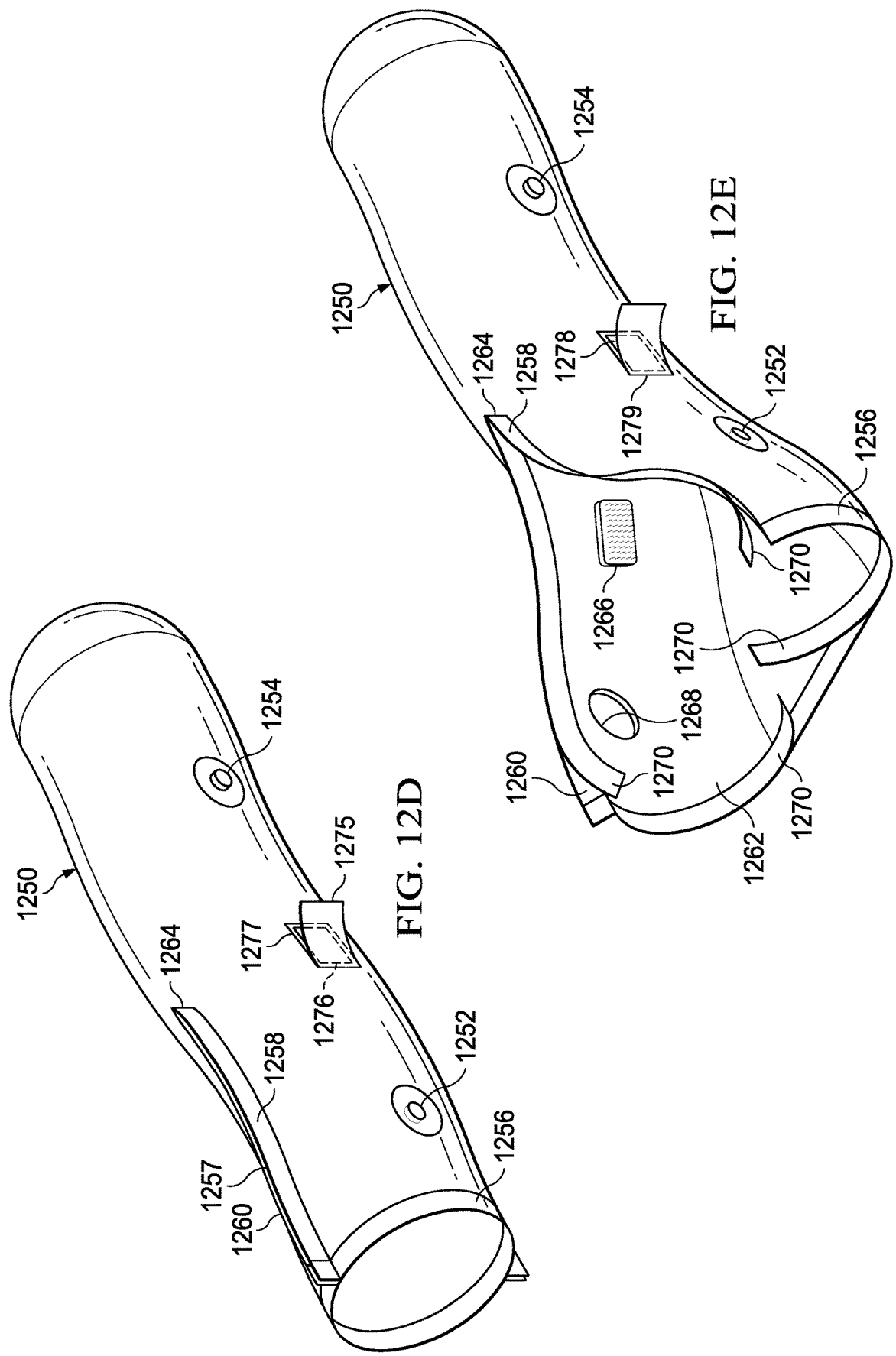

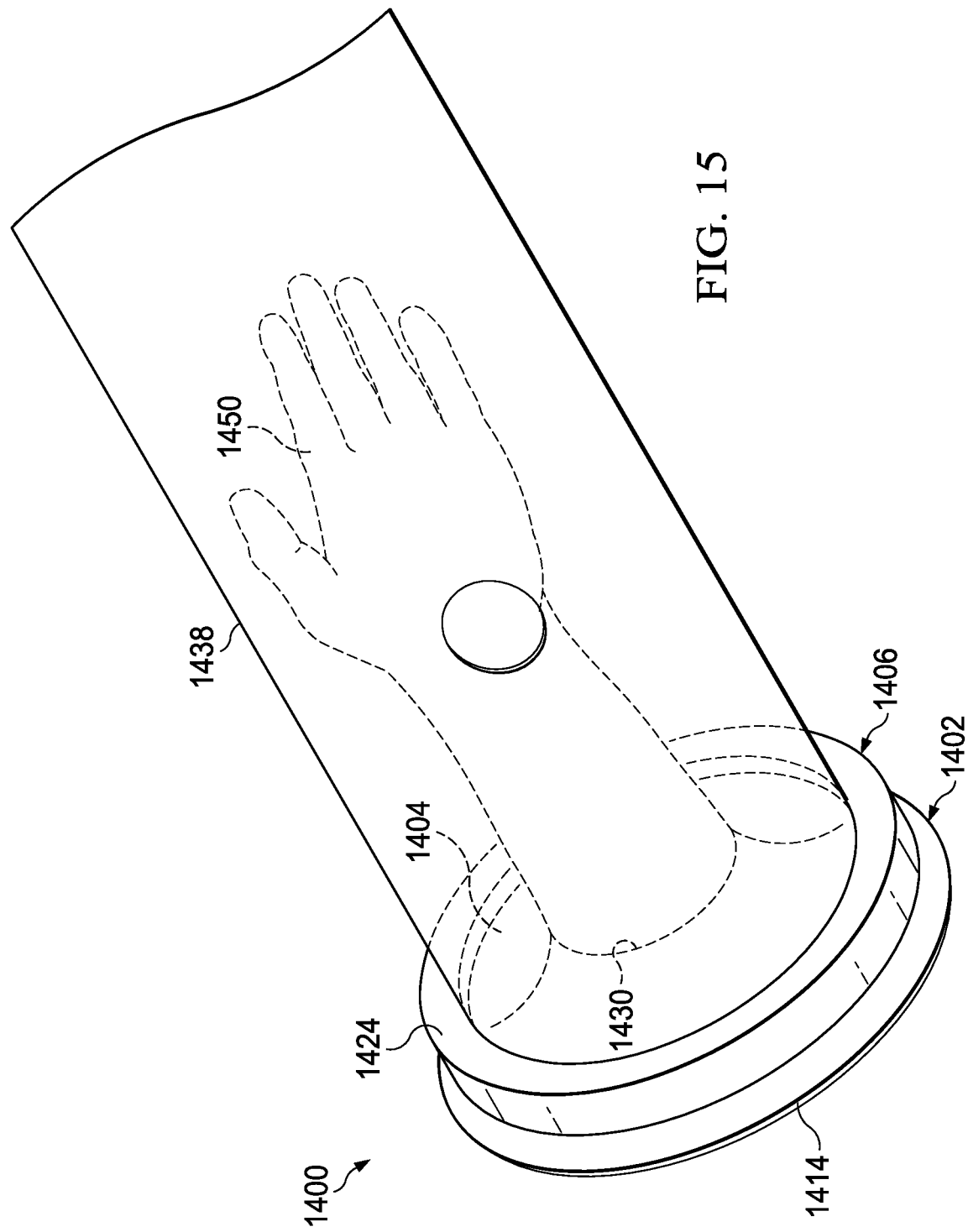

APPARATUS AND METHOD FOR DEPLOYING A SURGICAL PREPARATION

CROSS REFERENCE TO RELATED APPLICATION

This application is a continuation in part of application Ser. No. 15/459,690, filed Mar. 15, 2017, which is a continuation in part of application Ser. No. 15/005,750, filed Jan. 25, 2016, now U.S. Pat. No. 10,188,842, which is a continuation in part of application Ser. No. 14/312,498, filed Jun. 23, 2014, now U.S. Pat. No. 9,409,005, which is a continuation in part of application Ser. No. 13/199,343 filed Aug. 26, 2011, now U.S. Pat. No. 8,758,310, which is a continuation in part of application Ser. No. 11/602,542 filed Nov. 21, 2006, now U.S. Pat. No. 8,403,898.

FIELD OF THE INVENTION

This present invention relates to a method to an apparatus and method for applying antiseptic prior to surgery, cleaning wounds prior to, during, and after surgery, and providing care to a wound while it heals.

BACKGROUND OF THE INVENTION

Surgical site infections are frequently caused by bacteria commonly found on the surface of the skin. Since 1867, when Joseph Lister discovered the link between microbes and patient mortality after operations, he coined the term "antiseptic" after discovering that certain surgical preparations could be applied before surgery to eliminate bacteria. Practitioners have used aseptic techniques to reduce post-operative infections ever since.

In order to reduce bacteria, antiseptics are used prior to conducting the surgery to clean and disinfect the surgical site. Types of antiseptics include alcohols, iodine or iodine-containing compounds and chlorhexidine gluconate among others. There are two primary types of iodine-containing compounds, tincture of iodine, and iodophors. Tincture of iodine is an alcohol solution and was one of the first antiseptics used. However, iodophors or chlorhexidine and alcohol solutions are more commonly used today to prepare a surgical site for surgery.

The most common aseptic technique for disinfecting a surgical site requires application of an antiseptic solution immediately prior to the surgical procedure in the sterile operating theater after the patient has been anesthetized. When performing surgery to the extremities, i.e., leg or arm, the entire extremity is typically cleaned with the antiseptic solution. A sponge is immersed in the antiseptic solution, then applied to an area of the extremity with a scrubbing action and then discarded. A new sponge is immersed into the antiseptic solution and applied to a different area of the extremity. This process is then repeated until the entire area has been scrubbed. The scrubbing action physically dislodges bacterial colonies. Once the scrubbing is completed, another antiseptic solution is reapplied with a sponge in a painting action using a new sponge with each repeated application. After this procedure the surgical personnel must wait at least five to seven minutes before beginning the surgical procedure. The delay is required to allow the antiseptic solution to disinfect the surgical site.

There are several problems with the prior art procedure for disinfecting a surgical site. During the application of the antiseptic solution to the extremity, numerous sponges are required to be used and discarded, thus creating waste that must be handled and properly discarded. There is also a possibility that the surgical site will not be completely covered, thus creating a potential for bacteria and other contaminants remaining during surgery and serving as a potential source for post-surgical infection. The application of the antiseptic solution is prone to splashing and uncontrolled spills. Excess antiseptic solution spills create a potential safety hazard.

The prior art procedure for applying the antiseptic solution is also costly and time consuming. Operating theaters are expensive to maintain and operate. The time that the antiseptic solution takes to be effective costs the patient and the hospital a significant amount of money. The delay also slows the throughput of the operating theater, thereby raising the cost of the procedure to the hospital and the operating staff.

The prior art procedure puts the patient at an increased risk of morbidity and mortality by increasing the amount of time the patient is under anesthesia.

The current invention provides a device and method for applying an antiseptic solution to a surgical site prior to surgery, but outside the operating theater thus reducing anesthesia time along with operating room time and cost. The invention also contains the spills and reduces waste. Since the application of the antiseptic can be accomplished outside the operating theater, additional time and care can be used in applying the antiseptic, thereby reducing post-surgical infection.

Various prior art devices and methods have been used in the past to cover a wound, protect a wound site, or apply medicine to a wound site. But none of the prior art has been used to streamline application of a surgical antiseptic prior to surgery.

For example, U.S. Pat. No. 2,661,739 to Caskey discloses a casing which is made from elastic material to fit against an extremity to hold an absorbent material against a wound. The casing is surrounded by a fabric jacket to hold the casing and absorbent material in place and exclude contamination from the environment. However, the casing is only disclosed to be used after a wound has occurred and it does not disclose using the device to pre-treat an area prior to surgery. Additionally, it does not allow for the scrubbing of medicine against the skin through the device.

U.S. Pat. No. 6,992,233 to Drake, et al. discloses a delivery system for a flowable medicine to a wound in a confined area. Flowable medicine is contained in a strip which is adhesively applied to the skin such that the medicine is delivered to the wound. The flowable medicine is released when removable seal is removed. Drake does not disclose using the device for application of medicine prior to a wound occurring or to a large area of the body. It is limited to the area covered by the strip. Drake also does not disclose scrubbing the medicine against the skin through the device.

U.S. Pat. No. 6,664,434 to Cominsky discloses using a sealed bag around a wound to contain bodily fluids. The device includes an absorbent layer to absorb the bodily fluids exuding from a wound. It does not disclose using the bag prior to the wound or introduction of an antiseptic fluid within the bag. It also does not disclose the scrubbing of an antiseptic through the device.

The prior art fails to disclose or suggest a surgical solution application for preparing a patent's skin prior to surgery. Therefore, it is desirable to have a device and method for facilitating application of antiseptic solution in a non-sterile environment.

Preparation for surgery often includes wound management immediately after trauma. For example, wounds can occur in various locations with various environmental conditions. Wounds may occur with a significant amount of debris or airborne contaminants present. The ability of emergency response personal to remove debris from a wound as soon as practicable, apply antiseptic to the wound and surrounding areas to remove bacteria, and thereafter protect the wound from further contamination until the patient can receive additional medical attention can reduce the chance of infection and reduce the work required once the patient reaches the medical facility.

The current invention provides a method and apparatus to immediately treat wounds in the field before surgery to forestall infection and provide emergency care in a sterile environment before transportation to the surgical center.

Various prior art devices and methods have been used in the past to provide wound management through the use of an enclosure during debridement procedures, but none have been entirely successful.

For example, U.S. Publication No. 2004/0171998 to Marasco provides for an enclosure bag attached to a body portion which includes an inlet snorkel and a collection bag. However, the invention of Marasco is hampered because the bag is required to be connected to the drainage container through the discharge tube. Further the invention of Marasco fails to accommodate large wounds due to the configuration of the open end which restricts the size of the opening.

Similarly, U.S. Pat. No. 8,568,375 to Marasco discloses a wound treatment arrangement which discloses a connector between a debridement tool and a bag. However, the connectors disclosed do not easily accommodate rotation or angular translation of the debridement tool within the bag, nor is there provision made for scrubbing appliances within the bag.

U.S. Pat. No. 4,376,437 to Sundheim discloses an enclosure for treating human extremities for the treatment of arthritis, related muscular skeletal disorders, burns and wounds of generalized skin eruptions, for the control of temperature and chemical environments. However, no accommodation is made for sealing the enclosure against outside debridement tools or for scrubbing any wound contained by the enclosure.

The current invention has further applications in clinical wound management after surgery or the treatment of other infections wounds. For example, many wounds need to remain open to heal rather than be closed surgically. These wounds often need to be cleaned through debridement. Lavage systems introduce liquids, typically saline, either with or without other medications, into an open wound for cleaning and simultaneously suction the exhaust for proper disposal. Hospitalization is generally required for debridement procedures. Further, repeated debridement procedures are often required over a period of weeks or months, greatly increasing cost.

The current invention provides a method to clinically treat infectious wounds after surgery or that occur from other natural causes. Use of the current invention provides the advantage of allowing the patient to leave the hospital while still protecting the wound from contaminants and further allows easy access for repeated cleaning procedures. Use of the current invention also accommodates rotation and angular translation of various debridement tools thereby reducing unnecessary movement and wrinkling of the application bag.

The current invention can further be used to help with wound management by allowing for cleaning of surrounding skin during the healing process, including before or after negative pressure therapy.

SUMMARY

A surgical preparation solution applicator is described for preparing a patient's skin for surgery prior to entering the surgical theater. More specifically, a device and method for facilitating application of antiseptic solution to a surgical site in a non-sterile environment is described.

The applicator, in one embodiment, includes a bag which is sealed on three sides and open on a fourth side. A resilient seal gasket is affixed to the open end of the applicator bag. The gasket fits snuggly around the patient's body forming a seal between the interior of the bag and patient's body. An antiseptic solution is then introduced into the application bag through either a port in the application bag, a solution deployment pouch within the application bag or through an opening between the gasket and the patient's body. Alternatively, the antiseptic solution may be deployed in the application bag prior to positioning the bag on the patients extremity. The gasket prevents the release of the antiseptic until removed.

The solution deployment pouch releases antiseptic into the bag once the gasket is secured. The pouch can take the form of a capsule in ducted communication with the application bag which is filled with the antiseptic solution. Other embodiments include one or more ports and/or one or more solution deployment pouches.

In another embodiment, the applicator bag employs other closing means to seal the open end of the application bag securely against the patient's body. This closing means can include but is not limited to a pressure inflatable cuff, a tourniquet, or a pressure strap fixed with a buckle or Velcro® closure.

In another embodiment, the application bag is open on two ends having a resilient seal gasket fixed at each end. In this embodiment, the patient's body is inserted through the seal gaskets at both open ends of the application bag.

In another embodiment, the application bag is suited well for use on a relatively flat area of the body, such as the back or abdomen. In this embodiment, the open end of the bag is secured to the patient with a disk-like adhesive strip. The adhesive strip temporarily adheres to the patient's body during the procedure and acts as a seal between the patient's body and the interior of the bag. After the adhesive is adhered to the patient's body, the antiseptic solution is released inside the application bag, either through a port or by a solution deployment pouch located inside the application bag.

At all places other than the seal gasket, the application bag is loose-fitting around the patient's body to allow the user to manipulate the bag freely and completely apply antiseptic around the body part being treated without breaking the seal of the gasket.

In the preferred embodiment, the application bag is used to disinfect the surgical site before the patient has undergone use of anesthesia. Because the patient is awake, the temperature of the antiseptic solution may be uncomfortable to the patient and increase surgery anxiety in the patient. For this reason, the invention further provides an inexpensive mechanism to monitor the temperature of the antiseptic solution prior to application to the patient. Matching the temperature of the antiseptic solution to the patient aids in reducing pre-surgery anxiety of the patient and therefore a more efficient application of the antiseptic solution.

In yet another preferred embodiment, sterile sponges or other devices used to apply the antiseptic solution to the body can be contained in sealed pouches secured to the inside of the application bag or inside the antiseptic pouch.

When the antiseptic is deployed within the bag, the sterile sponges are used to apply the bag and then discarded with the bag prior to surgery.

After this process has been completed, the application bag contains the antiseptic and prevents outside bacteria and contaminants from contacting the treated area. The application bag is designed to remain in place until the patient is positioned in the operating theater. The application bag is removed immediately prior to surgery.

In another embodiment, the application bag is suited well for use on an extremity, preferably a leg. In this embodiment, the application bag is generally shaped to fit around the extremity. The application bag is secured to the extremity with any of, but not limited to, the aforementioned securing means. The application bag further has a plurality of holes, preferably at the anterior knee area and both sides of the ankle to accommodate the attachment of a scrub brush. The application bag has an antiseptic insertion means that includes, but is not limited to, the aforementioned antiseptic means.

The scrub brush includes a brush and a collapsible handle connected to the brush. The brush includes bristles attached to a scrubbing surface. The brush is attached to the inside surface of the application bag at one of the plurality of holes. The collapsible handle is connected to the brush protruding through the application bag allowing a user to move the scrub brush without the user contacting the patient's skin.

In another embodiment, the application bag is comprised of two releasable halves connected to a resilient seal gasket. In this embodiment, the patient's extremity is inserted through the gasket and positioned upon a first half of the application bag. The second half of the application bag is then aligned with the first half of the application bag. The two halves of the application bag are releasably affixed to each other proximate the perimeter of each half using common in the art means such as releasable adhesive or a resealable zipper connection. An antiseptic solution is then introduced into the application bag through either a port in the application bag, a solution deployment pouch within the application bag or through an opening between the gasket and the patient's body. Removal of the application bag is accomplished by peeling away the first half of the bag from the second half of the bag using a tab extending from either or both halves of the bag In another embodiment, the application bag is used to reduce the risk of infection immediately after trauma. The application bag is positioned adjacent a wound site. Antiseptic is then introduced through a port in the application bag or solution deployment pouch within the application bag.

In another embodiment, the application bag contains two ports. The ports are sealed by caps which allow the introduction of antiseptic but also allow for the connection of a lavage system to the application bag for the cleaning and debridement of an open wound and for removal of the cleaning solution. In this embodiment, a separate flexible container is provided for storage and disposal of cleaning fluid after use.

In another embodiment, the application bag includes a resealable flap. The flap allows for access to the wound that is not available otherwise.

In another embodiment, the application bag includes an elongated resealable section immediately adjacent the opening for the extremity. In this embodiment, the application bag may be opened more completely to receive extremities with large wounds or which are immobile due to trauma or surgery.

In another embodiment, the application bag connector includes a rotary coupling which is adapted to accommodate a lavage wand for debridement procedures in order to allow complete and free rotation of the lavage wand.

In another embodiment, the application bag includes a gasket which is adapted to include a tourniquet for application of pressure to an extremity for use in emergency procedure in the field.

BRIEF DESCRIPTION OF THE DRAWINGS

In the detailed description of the preferred embodiments presented below, reference is made to the accompanying drawings.

FIG. 11E is an exploded perspective view of a preferred embodiment of a removable scrub brush and docking fixture.

FIG. 12D is a perspective view of a preferred embodiment showing an elongated opening in a "closed" configuration.

FIG. 12E is a perspective view of a preferred embodiment showing an elongated opening in an "open" configuration.

FIG. 15 is a perspective view of an embodiment of the invention showing the use of an alternate sealing means.

DETAILED DESCRIPTION

Figure 1A:
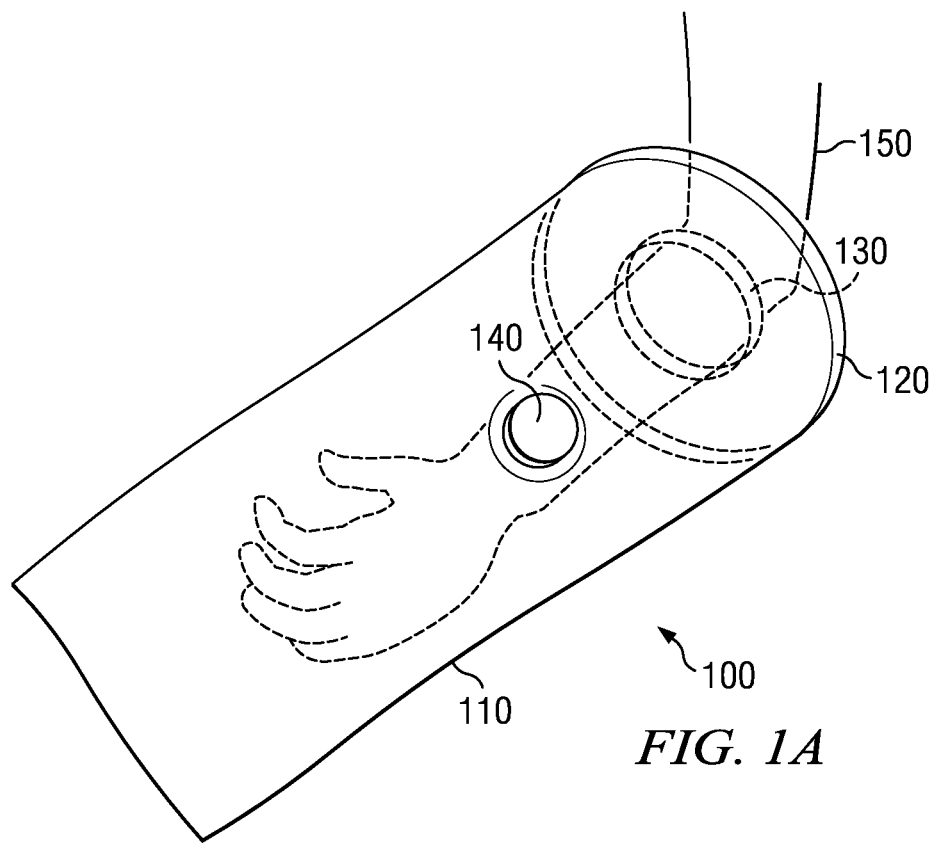
FIG. 1A is a perspective view of an embodiment of the invention showing the use of a flat neoprene gasket seal.

FIG. 1A shows a preferred embodiment of solution applicator 100. Solution applicator 100 includes application bag 110. In the preferred embodiment, application bag 110 is made of HDPE (high density polyethylene) which is typically translucent, but not fully transparent. In other embodiments, the application bag can be made out of LDPE (low density polyethylene) and can be quite clear, but still not totally transparent. In other embodiments, LLDP (linear low density polyethylene) can be employed where a higher structural rigidity is required by the cleaning process. Other flexible sheeting can be used so long as it is inert with respect to the antiseptic solution.

In another preferred embodiment, the interior and/or exterior of the application bag can be textured to increase the effectiveness of the application of the antiseptic to the patient. If on the exterior of the application bag, the purpose of the texturing is to increase friction between the hands of the user and the exterior of the application bag to aid in manipulation of the application bag during use. If on the interior of the application bag, the textured surface is useful in scrubbing the surgical site to remove bacterial colonies. Examples of textures can include raised ribs, chevron patterns, diamond patterns or random "crinkling." Other plastics can be used if complete transparency is required for various cleaning processes. In other embodiments, the application bag can be color coded to indicate different sizes, different antiseptics contained within the bag or the proper operating theater for the patient.

In a preferred embodiment, application bag 110 can be formed from two identical or nearly-identical sized sheets. Both sheets will have the same or nearly the same shape. In a preferred embodiment, the two sheets are rectangular. All of the sides but one are sealed or fused by an adhesive or heat welding as known in the art, leaving the remaining side open. The flat format of the completed application bag increases the ease of storage and/or deployment of the bag from a roll or cardboard box as known in the art. The shape also promotes economy of manufacture.

In another preferred embodiment, application bag 110 can be formed by a flexible tubular extrusion of plastic. After manufacture, the tube can then be cut to length. After being cut, one end is sealed or fused by known inductive welding means leaving the other end open. Other preferred embodiments can include frustoconical shapes, inverted frustoconical shapes and generally spherical shapes.

Different parts of the body can be decontaminated. In FIG. 1A, patient's appendage 150 is shown surrounded by solution applicator 100. The dimensions of the application bag vary depending on the part of the body being decontaminated. Application bag 110 should fit loosely around the body part placed inside application bag 110.

In the preferred embodiment, the general circumference of application bag 110 is at least 2 inches larger than the part of the body being decontaminated. The width of application bag 110 in a preferred embodiment is usually between 2 inches and 40 inches. In the preferred embodiment, the general length of the application bag is at least 2 inches longer than the part of the body being placed in application bag 110. The length of application bag 110 in a preferred embodiment would be between 2 inches and 60 inches. The application bag should also allow for complete articulation of any joint surrounded in order to allow for complete coverage by the antiseptic solution.

Figure 1B:
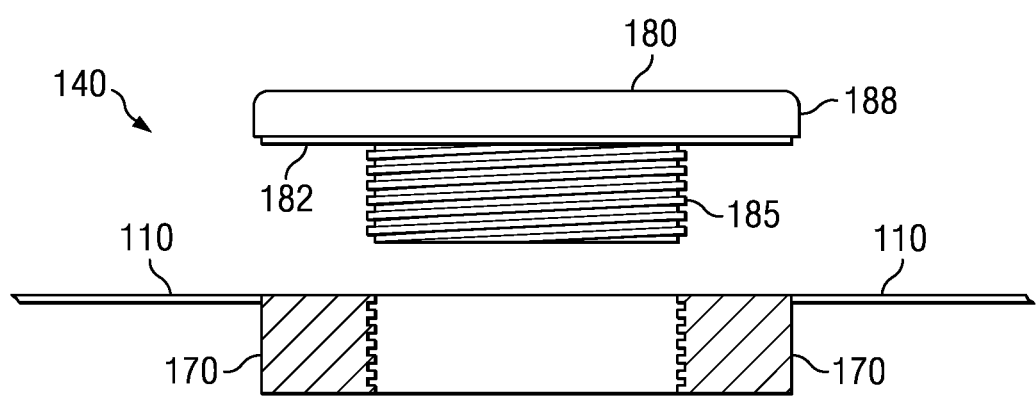
FIG. 1B is a cross sectional view of a preferred embodiment of fill/drain port.

In a preferred embodiment, application bag 110 also includes fill/drain port 140. Fill/drain port 140 allows for deployment of the antiseptic solution into the application bag and draining of excess antiseptic from the application bag. Fill/drain port 140 is located generally in a position to allow for deployment of the antiseptic solution to cover the extremity. FIG. 1B is an expanded view of a preferred embodiment of fill/drain port 140. Fill/drain port 140 includes lid 180. Lid 180 seals opening in application bag 110. Lid 180 includes four parts, cap 188, threaded section 185, flexible gasket 182 and port ring 170. Cap 188 is of such minimum height that it can be easily grasped to open fill/drain port 140. Threaded section 185 width can vary in size between ¼ inch and 4 inches. Threaded section 185 is threaded to match port ring 170.

Port ring 170 is attached to opening in application bag 110 by a known adhesive or heat welding. Port ring 170 is threaded to receive threaded section 185. Port ring 170 is approximately the same depth as the threaded section 185. In the preferred embodiment the depth is between about ¼ of an inch to about 3 inches. A flexible gasket 182 is provided to seal the lid against the port ring. When lid 180 is threaded into port ring 170, bottom of lid 180 fits flush and seals against of port ring 170.

Fill/drain port 140 can be constructed from any commercially available plastic, including but not limited to polypropylene, polyethylene, or polystyrene. In other embodiments, the fill/drain port can be fitted with a quick release mechanism for removal of the antiseptic with a pump through a hose and connection fitting. Other non-threaded resealable cap and base configurations will also suffice.

Attached to open end of application bag 110 is gasket 120. Open end of application bag 110 is affixed to gasket 120 through a known adhesive or heat welding. Gasket 120 can be manufactured from synthetic rubber, such as neoprene, or a resilient plastic polymer. The gasket color can be coded to indicate the size and/or shape of the bag making for easy and error free deployment of the antiseptic solution.

Gasket 120 has hole 130 in the relative center of gasket 120. Patient's appendage 150 is inserted through hole 130 and into application bag 110. In the preferred embodiment, diameter of hole 130 ranges between about 1 inch and 15 inches. However, those skilled in the art will recognize that other sizes can be provided to accommodate different patients and circumstances. Hole 130 should fit around the body extremity such as to prevent the antiseptic solution from escaping application bag 110 when in use.

Figure 2:
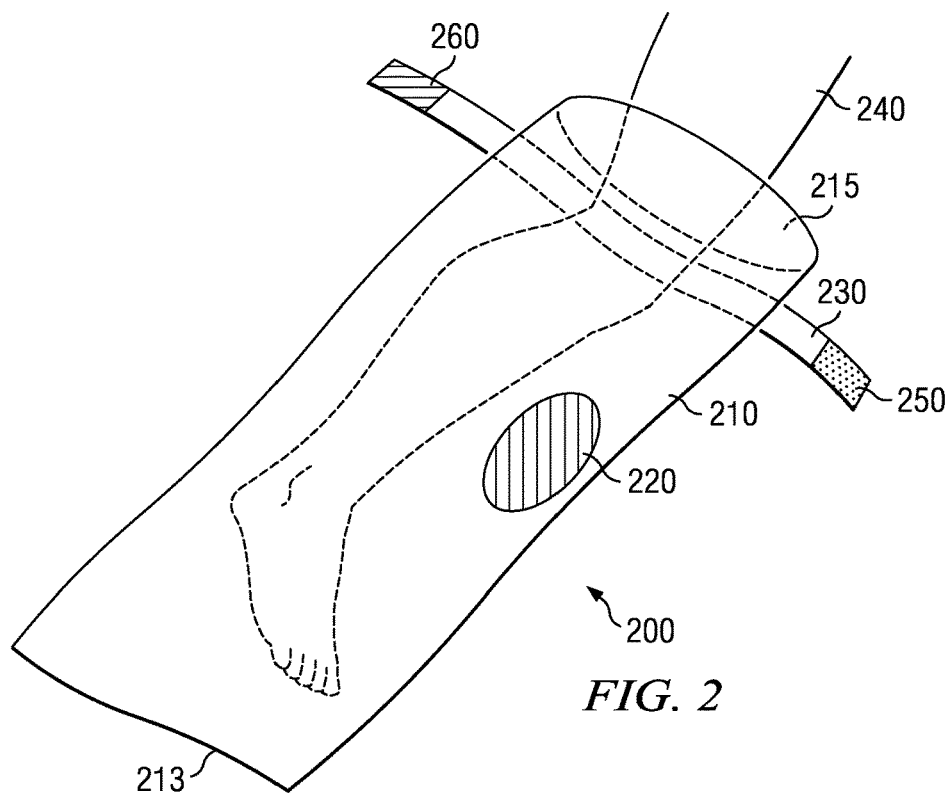
FIG. 2 is a perspective view of a preferred embodiment of the invention showing an alternate closing means.

FIG. 2 shows another preferred embodiment of solution applicator 200. Solution applicator 200 includes application bag 210 which has larger dimensions to accommodate a larger appendage such as a leg. Patient's appendage 240 is inserted into application bag 210 through opening 215 toward closed end 213. This embodiment includes solution deployment pouch 220 and a different closing means.

Application bag 210 is secured around patient's appendage 240 through the use of closing means 230. Some examples of closing means include an elastic band, adhesive tape or strap with a buckle or Velcro® closure. A preferred embodiment includes strap with a Velcro® closure. Closing means 230 allows for securing and sealing application bag 210 around varying size appendages and easy adjustment. Velcro® closure includes hook section 260 and receiver section 250 as necessary to use the closing means 230 as described.

Closing means 230 is located between the opening 215 of application bag 210 and the area to be treated with antiseptic, such that the area to be treated with antiseptic is contained within application bag 210. Closing means 230 can be attached to application bag 210 by commercially available adhesive or can be detachable.

Solution deployment pouch 220 is located on the interior of application bag 210 and contains the antiseptic to be deployed. Solution deployment pouch 220 can vary in size and shape depending on the amount of antiseptic solution contained. In the preferred embodiment, the solution deployment bag contains 2.5 liters of antiseptic solution. The solution deployment pouch may be color coded to indicate the type of antiseptic contained or may be metalized to prevent light from entering the pouch to the detriment of the antiseptic solution. In the preferred embodiment, the antiseptic to be deployed is chlorhexidine, sold under the trademark ChloraPrep® and available from Medi-Flex, Inc. of Leawood, Kans. However, other antiseptics that are effective without evaporation can also be employed.

Figure 3A:
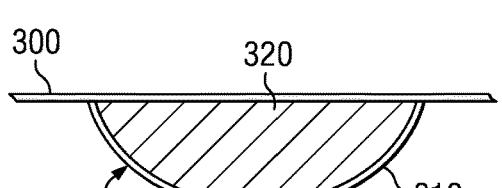
FIG. 3A is cross sectional view of a preferred embodiment of an antiseptic pouch attached to the interior of the application bag.
Figure 3B:
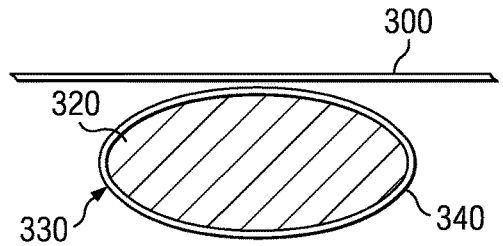
FIG. 3B is a cross sectional view of a preferred embodiment of the invention showing an antiseptic capsule attached to the interior of the application bag.

FIG. 3A and FIG. 3B illustrate two preferred embodiments for solution deployment pouch 220. As shown in FIG. 3A, a cavity 305 is created on the inside of application bag 300 by use of a cavity cover 310. The cavity cover 310 in the preferred embodiment is a hemispherical flexible container heat welded around its circumference to the interior of the application bag. The size of cavity cover 310 will depend on the amount of antiseptic solution 320 to be contained. Cavity cover 310 is of such strength that cavity cover 310 can be ruptured for use but not during normal handling and storage of the application bag. Cavity cover 310 in the preferred embodiment is formed from a 3 ml plastic sheet made of HDPE. When cavity cover 310 is ruptured, antiseptic solution 320 located in the deployment pouch is released to the interior of the application bag.

FIG. 3B shows another preferred embodiment of solution deployment pouch 220. Antiseptic solution 320 is encapsulated in capsule 330. Size and shape of capsule 330 will vary depending on the amount of antiseptic solution 320 contained. Capsule cover 340 forms the outer casing of capsule 330 and encapsulates antiseptic solution 320. Capsule 330, and the encapsulated antiseptic 320, are attached to the inside of application bag 300 by a known adhesive or spot welding. Capsule covering 340 can be manufactured from commercially available plastics. In the preferred embodiment, the covering is HDPE and is about 3 ml thick. In another embodiment, the capsule can be a rigid but frangible plastic capsule contained in a cylindrical form capable of being broken for use through a set of central perforations. Capsule 330 can be attached to application bag 300 at the time of shipment to the user or could be sent separate from the application bag 300 and the user attaches capsule 330 at the time of use.

Multiple capsules or pouches can be used in a single application bag depending on the decontamination method being addressed. Further, differing antiseptic solutions can be contained in different capsules. Furthermore, sterile sponges, brushes, gauze and swabs can be contained in the capsule at the time of manufacture for use within the application bag to scrub the surgical site.

Figure 3C:
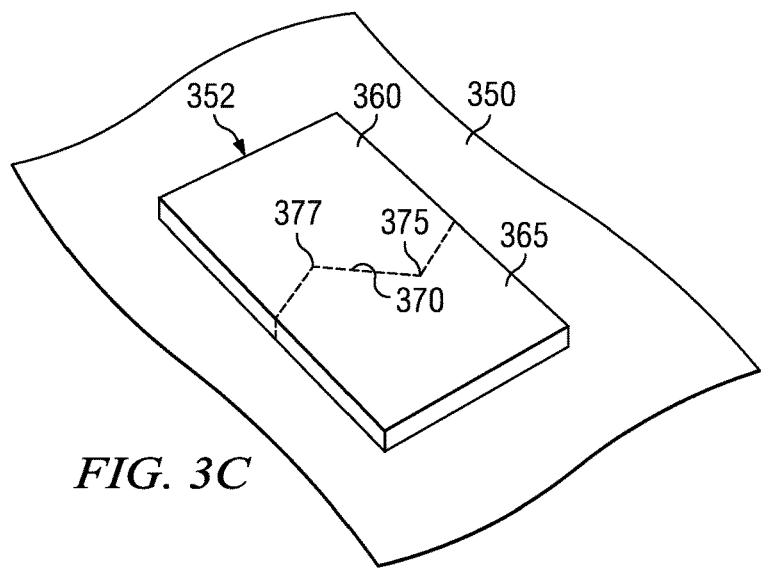
FIG. 3C is a perspective view of a puncturing device used in a preferred embodiment of the invention.

Referring now to FIG. 3C, a puncturing device is shown used in the preferred embodiment of the invention which allows for easy puncturing of the deployment pouch and/or temperature monitoring. The surface of the deployment pouch is shown as 350. Fixed to the external surface of deployment pouch 350 is a rigid plastic rectangle 352. In the preferred embodiment, the dimensions of the plastic rectangle are approximately 10 ml thick and formed of a rigid polystyrene. Other rigid plastics or light metals such as aluminum can be used as well. Plastic rectangle 352 includes halves 360 and 365 separated by a perforation 370. Perforation 370 in the preferred embodiment traverses the rectangle in an angled fashion, including two pointed extensions 375 and 377. In another preferred embodiment, the deployment pouch may be a frangible capsule, which may be broken to deploy an antiseptic solution.

In use, plastic rectangle 352 is broken along perforation 370 separating the two halves 360 and 365. Pointed extensions 377 and 375 are then available to breach the surface of deployment pouch 350 thereby allowing the antiseptic fluid contained to escape into the application bag. The advantage of the use of plastic rectangle 352 is to allow controlled dispersion of the antiseptic fluid and to allow a thicker and more robust flexible plastic to be used for the deployment pouch.

In yet another embodiment, plastic rectangle 352 can include a temperature sensitive dye. The temperature sensitive dye can be used to indicate the temperature of the antiseptic contained in the deployment pouch to allow for an accurate and effective dispensing temperature or for patient comfort.

Figure 4:
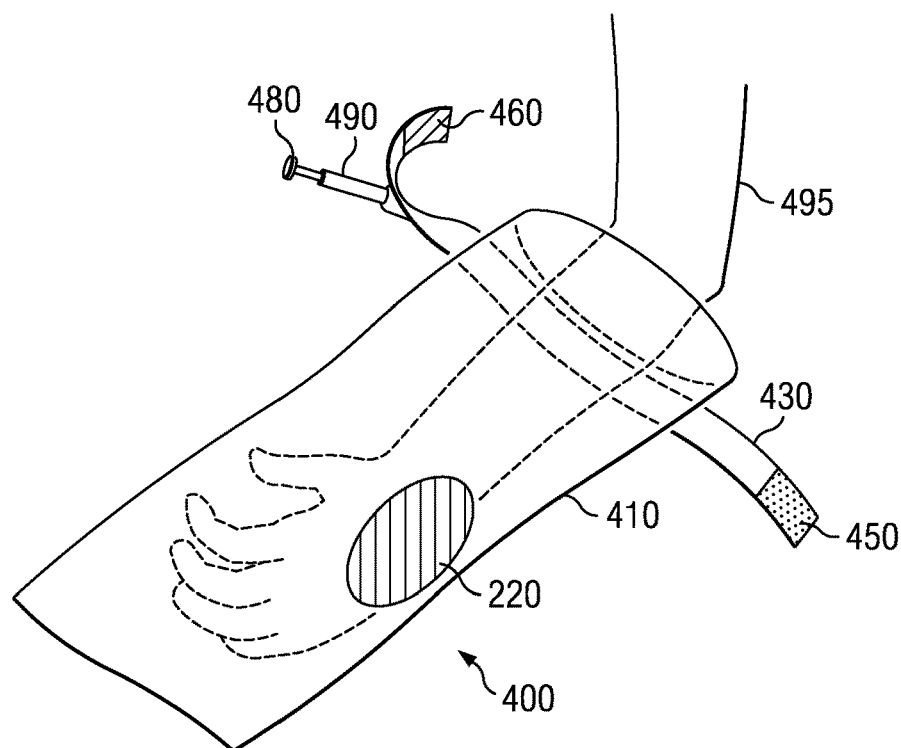
FIG. 4 is a perspective view of a preferred embodiment of the invention showing an alternate closing means.

FIG. 4 shows yet another preferred embodiment of invention. Solution applicator 400 is application bag 410 with one end sealed and one end open. Patient's appendage 495 is placed inside application bag 410 through the open end.

In this embodiment, application bag 410 is closed around patient's appendage 495 by use of pressure inflatable cuff 430. Pressure inflatable cuff 430 can be secured by any appropriate closing means 450 and 460. Specifically, a preferred embodiment for such closing means 450 and 460 is Velcro®, wherein closing means 450 is hook section and closing means 460 is receiver section. Pressure inflatable cuff 430 is located adjacent the open end of application bag 410. Pressure pump 480 inflates pressure inflatable cuff 430 through pump 490. Pressure pump 480 can be manually or mechanically inflated by means of a hand pump or electrical pressure pump. Pressure inflatable cuff 430 when inflated creates a seal sufficient to prevent the antiseptic from escaping application bag 400. The cuff can also be inflated to the point where it acts as a tourniquet about the effected appendage.

Figure 5:
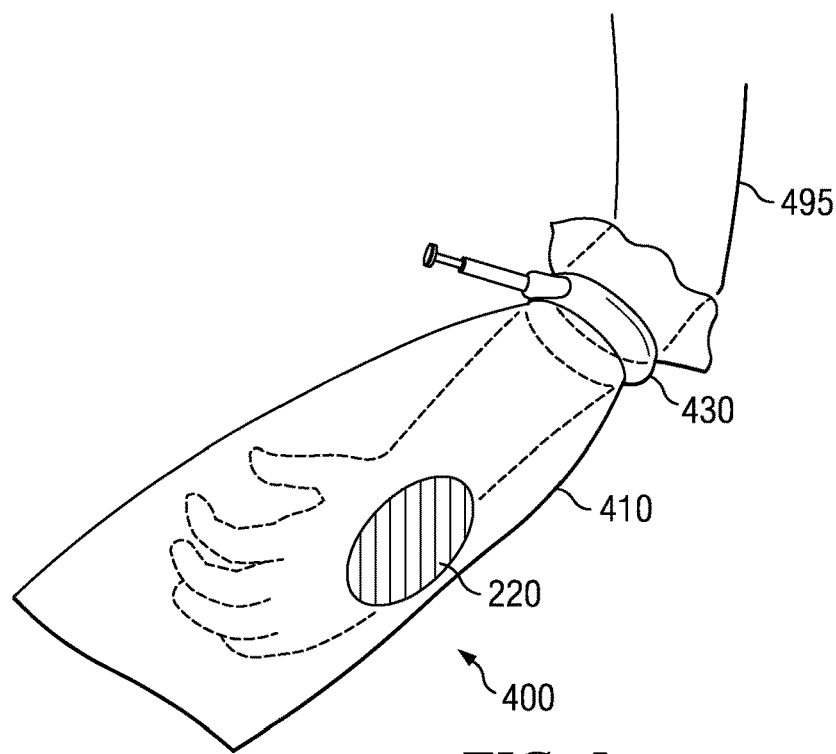
FIG. 5 is a perspective view of a preferred embodiment of the invention disclosed.

FIG. 5 illustrates solution applicator 400 when pressure inflatable cuff is inflated.

Figure 6:
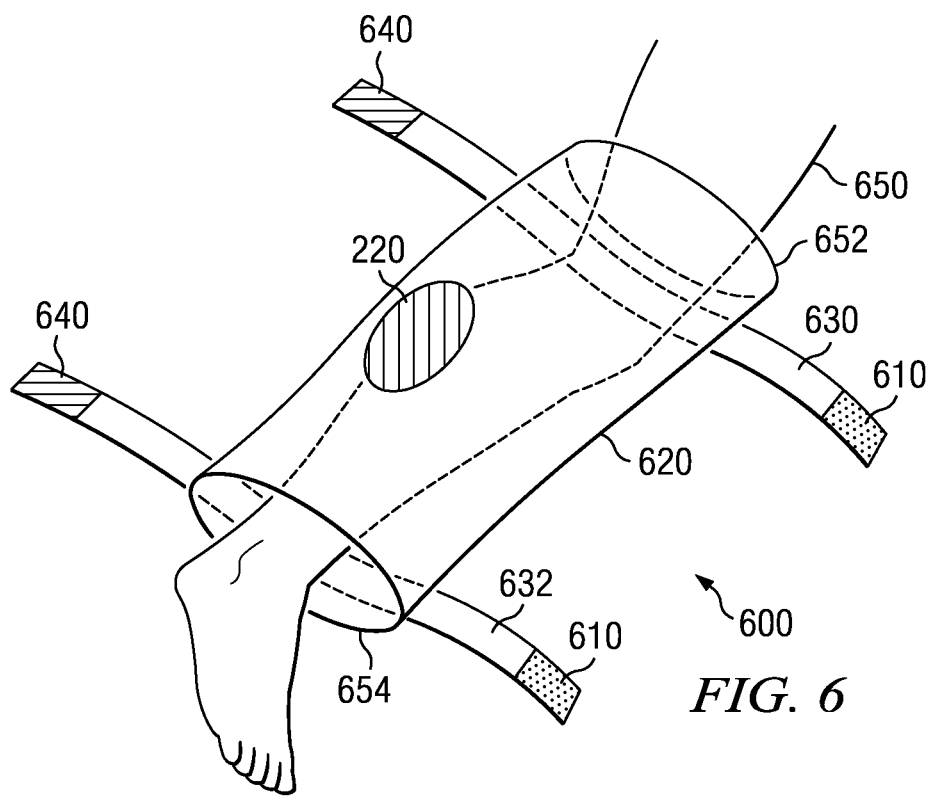
FIG. 6 is a perspective view of a preferred embodiment of the invention showing the use of two closing means.

FIG. 6 shows yet another preferred embodiment of solution applicator 600. This embodiment can be employed when only a section of a patient's appendage 650 is to be treated with antiseptic. In this embodiment, application bag 620 is open at both ends 652 and 654 and is tubular. The length of application bag 620 can vary depending on the size of the area being treated.

Each end of application bag 620 is closed around patient's appendage 650 by use of closing means 630 and 632. Each closing means is similar to those embodiments already described. For example, if Velcro® is used to secure closing means 630 and 632, Velcro® closure includes hook sections 640 and receiver sections 610 as necessary to use the closing means 630 and 632 as described. Solution deployment pouch 220 is adhered to the inside of application bag 620 between the closing means on either end.

Figure 7:
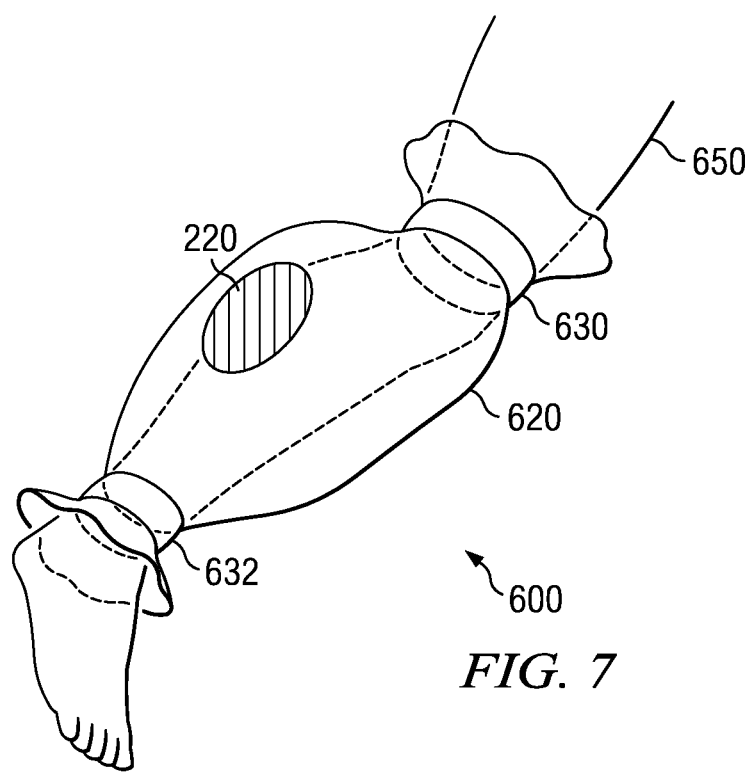
FIG. 7 is a perspective view of a preferred embodiment of the invention showing two closing means.

FIG. 7 illustrates solution applicator 600 after each end of application bag 620 has been closed around patient's appendage 650. The portion of application bag 620 between closing means is loose-fitting around patient's appendage 650. Solution deployment pouch 220 is ruptured and antiseptic fluid escapes to be massaged into the skin. All excess antiseptic is retained in the application bag 620 until closing means 630 and 632 are released and application bag 620 is removed.

Figure 8:
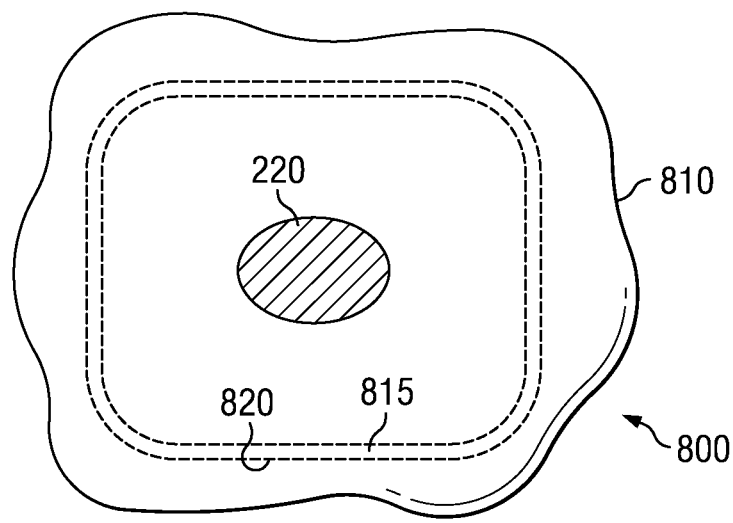
FIG. 8 is a plan view a preferred embodiment of the invention.

FIG. 8 shows a preferred embodiment of solution applicator 800. Solution applicator 800 can be used to apply antiseptic to a relatively flat area of the body, such as the abdomen or back. Application bag 810 forms a generally hemispherical shape placed over the surgical site. In the preferred embodiment, application bag 810 allows a clearance of about 3 inches when attached to the patient.

The circumference of application bag 810 is lined with a disk-like adhesive strip 815. The adhesive strip is of sufficient tackiness to adhere to form a seal with the patient's skin, but still removable without injury. Suitable adhesives are well known in the art. The width of the adhesive strip should range between ¼ inch and 1 inch. In the preferred embodiment, a removable waxed tape covers the adhesive strip until such time as solution applicator will be applied to patient. Attached to the interior of application bag 810 is solution deployment pouch 220 which contains antiseptic for treatment of the patient. Deployment and use of the antiseptic fluid is similar to that described above.

Figure 9:
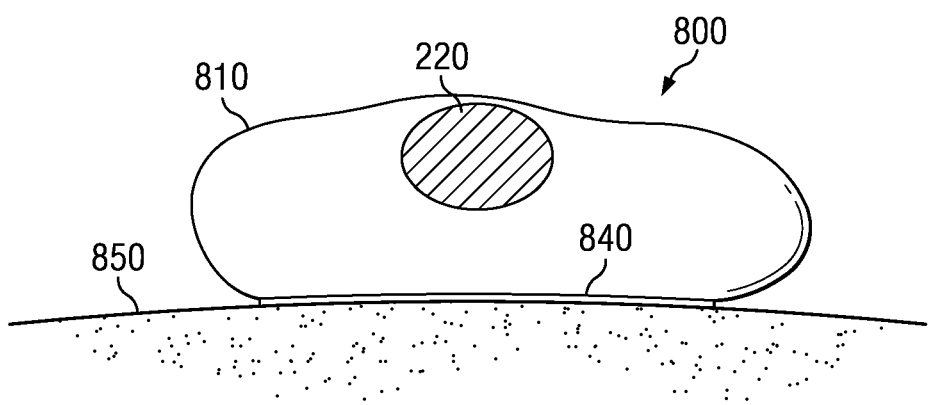
FIG. 9 is a side view of a preferred embodiment of the invention.

FIG. 9 illustrates a side view of solution applicator 800 attached to abdomen of patient 850. After adhesive strip 840 is applied to the skin of the patient, the remainder of application bag 810 allows for user to maneuver application bag 810 to rub or massage the antiseptic fluid over the skin without removing adhesive strip 840 from the skin.

Referring to FIGS. 10A, 10B, 10C, and 10D, application bag 910 has outside surface 914 and inside surface 915. Application bag 910 further has a plurality of holes 911, 912, and 913, to accommodate the attachment of a plurality of scrub brushes 900. Hole 911 is located generally at the anterior knee area. Holes 912 and 913 are located on opposite sides of the ankle area. Scrub brush 900 is attached to inside surface 915 by an adhesive or welding means known in the art. Handle 902 then protrudes through the holes 911, 912, and 913, extending past outside surface 914 to allow a user to move scrub brush 900 to scrub the patient's skin without the user making contact with the patent's skin.

Figure 10A:
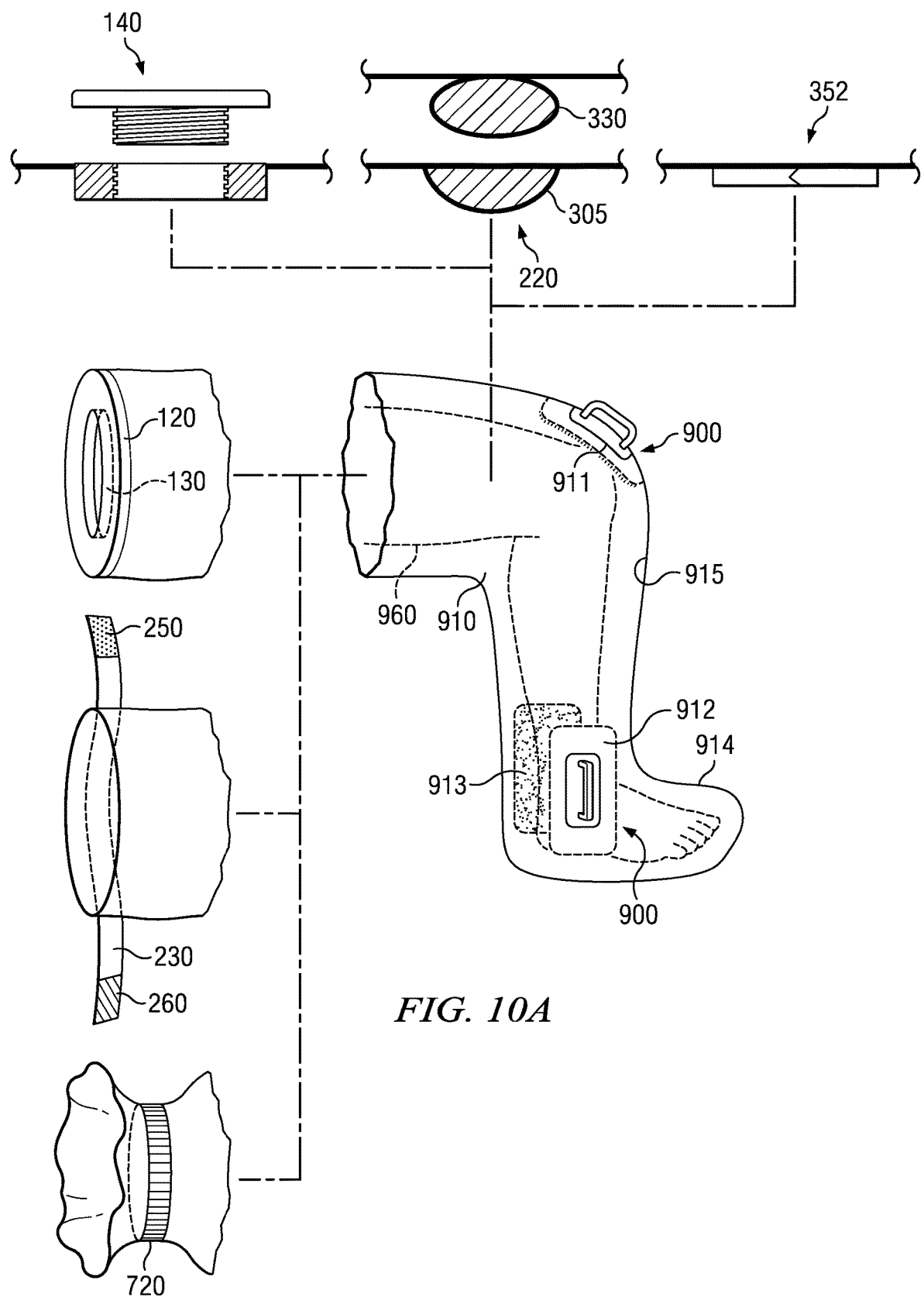
FIG. 10A is a side view of a preferred embodiment.
Figure 10B:
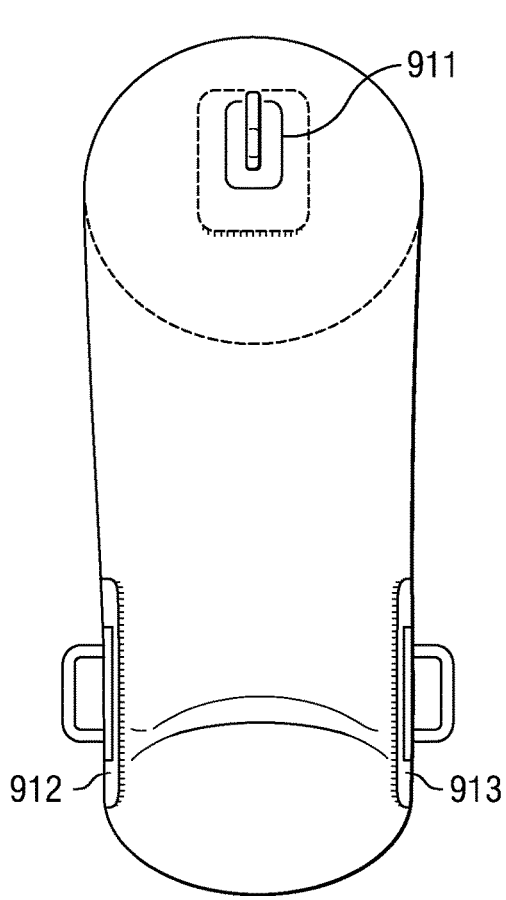
FIG. 10B is an end view of a preferred embodiment.
Figure 10D:
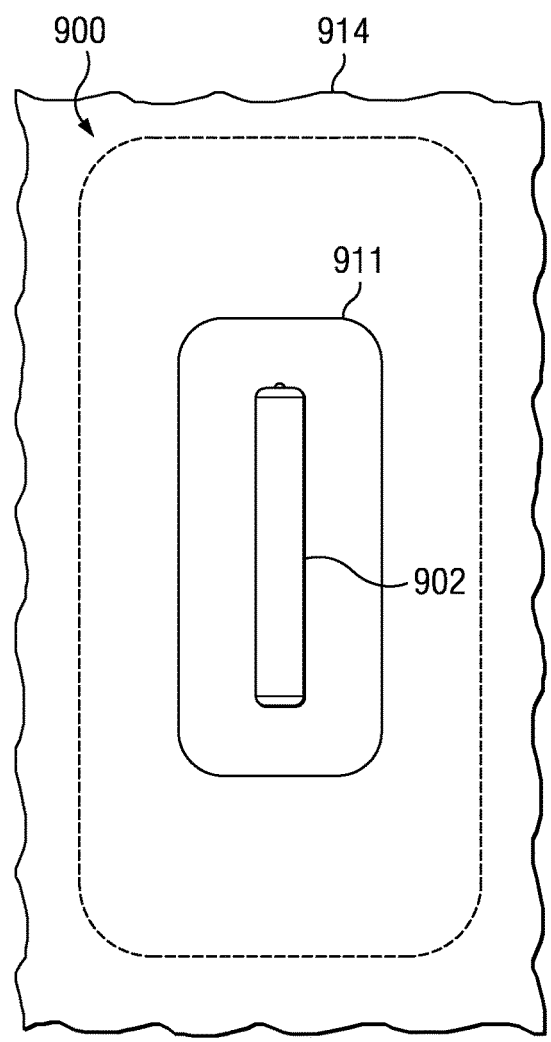
FIG. 10D is a detail top view of a preferred embodiment.
Figure 10C:
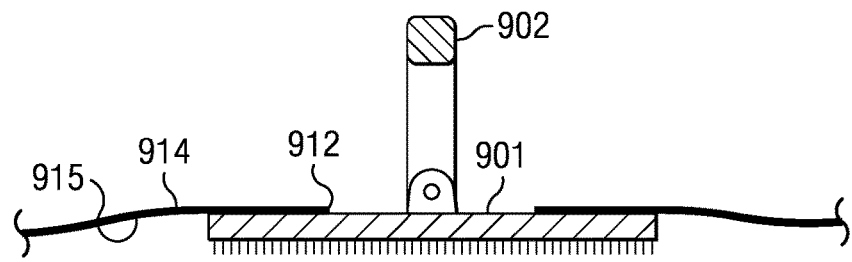
FIG. 10C is a partial section view of a preferred embodiment.

Referring to FIG. 10A, application bag 910 can include a multitude of sealing means including one of, but not limited to, the aforementioned gasket 120 with hole 130, closing means 230 with hook section 260 and receiver section 250, and elastic band 720.

Application bag 910 can include a multitude of antiseptic insertion means including one of, but not limited to, the aforementioned fill/drain port 140, solution deployment pouch 220 including cavity 305 and capsule 330, and plastic rectangle 352.

In a preferred embodiment, application bag 910 is shaped to generally match leg 960. In this embodiment, scrub brushes 900 are attached to application bag 910 at the anterior knee area and opposite sides of the ankle. However, those skilled in the art will appreciate that application bag 910 can be made in a multitude of shapes to generally match other extremities or adapted to fit a torso and scrub brushes 900 can be attached to application bag 910 at any desired location.

In a preferred embodiment, application bag 910 is made of HDPE (high density polyethylene) which is typically translucent, but not fully transparent. In other embodiments, the application bag can be made out of LDPE (low density polyethylene) and can be quite clear, but still not totally transparent. In other embodiments, LLDP (linear low density polyethylene) can be employed where a higher structural rigidity is required by the cleaning process. Other flexible sheeting can be used so long as it is inert with respect to the antiseptic solution. Other plastics can be used if complete transparency is required for various cleaning processes. In other embodiments, the application bag can be color coded to indicate different sizes, different antiseptics contained within the bag or the proper operating theater for the patient.

In another preferred embodiment, the interior and/or exterior of application bag 910 can be textured to increase the effectiveness of the application of the antiseptic to the patient. If on the exterior of the application bag, the purpose of the texturing is to increase friction between the hands of the user and the exterior of the application bag to aid in manipulation of the application bag during use. If on the interior of the application bag, the textured surface is useful in scrubbing the surgical site to remove bacterial colonies by applying an increased friction to the surgical site. In one embodiment, the textured surface may be used to scrub the surgical site and/or an area out of the reach of scrub brush 900. In one embodiment, the textured surface and, the surgical site or the out-of-reach area, has a higher friction coefficient than the interior surface and, the surgical site or the out-of-reach area. In one embodiment, the textured surface and the hands of the user has a higher friction coefficient than the exterior surface and the hands of the user. The harder the surgical site and/or the out-of-reach area is scrubbed with the textured surface, the higher the friction applied to the surgical site and/or the out-of-reach and vice versa. Examples of textures can include a set of raised ribs, chevron patterns, diamond patterns or random "crinkling" having a varying thickness. Any raised pattern that extends from the interior or outside surface may be employed. Other plastics can be used if complete transparency is required for various cleaning processes. In other embodiments, the application bag can be color coded to indicate different sizes, different antiseptics contained within the bag or the proper operating theater for the patient.

In a preferred embodiment, application bag 910 can be formed from two identical or nearly-identical sized sheets. Both sheets will have the same or nearly the same shape. All of the sides but one are sealed or fused by an adhesive or heat welding as known in the art, leaving the remaining side open. The flat format of the completed application bag increases the ease of storage and/or deployment of the bag from a cardboard box as known in the art. The shape also promotes economy of manufacture.

In another preferred embodiment, application bag 910 can be formed by a flexible tubular extrusion of plastic. After manufacture, the tube can then be cut to shape. After being cut, ends are sealed or fused by known inductive welding means leaving one end open.

In a preferred embodiment, the general circumference of application bag 910 is at least 2 inches larger than the part of the body being decontaminated. The width of application bag 910 in a preferred embodiment is usually between 2 inches and 40 inches. In the preferred embodiment, the general length of the application bag is at least 2 inches longer than the part of the body being placed in application bag 910. The length of application bag 910 in a preferred embodiment would be between 2 inches and 60 inches. Application bag 910 should also allow for complete articulation of any joint surrounded in order to allow for complete coverage by the antiseptic solution.

Referring to FIGS. 11A, 11B, 11C, and 11D, a preferred embodiment of scrub brush 900 comprises brush 901, and rotatable handle 902. Brush 901 includes bristles 903, which are attached to brush 901. Handle 902 is connected to brush 901 at connection brackets 904, 905, 906, and 907. Pins 908 and 909 are inserted into connection bracket 904 and 906 sliding through handle 902 into connection brackets 905 and 907.

Handle 902 can rotate about an axis adjacent to brush 901. Handle 902 can be moved from position 950, which is generally perpendicular to brush 901. Handle 902 can be moved in either direction 951 to rest on brush 901 at position 953, which is adjacent to brush 901. Alternatively, brush 902 can be moved in direction 952 to position 954, which is adjacent to brush 901.

In a preferred embodiment, brush 901 and handle 902 are constructed of a transparent plastic. Bristles 903 are also constructed of a flexible plastic. It will be appreciated by those skilled in the art that a multitude of transparent and durable materials may be substituted for the construction of scrub brush 900 so long as it is inert with respect to the antiseptic solution.

In a preferred embodiment, scrub brush 900 is attached to application bag 910 in each of holes 911, 912 and 913 with an adhesive or welding means known in the art. The adhesive is applied to form a seal around each scrub brush and each hole.

In use, application bag 910 including an antiseptic insertion means is raised to a temperature approximately equal to that of the patient. An indication of the proper temperature is shown by the color of the plastic rectangle included on the deployment pouch. The application bag is extended and placed around the surgical site. In a preferred embodiment, application bag 910 is secured around the proximal end of the extremity. The distal end of the extremity resides in the interior of the application bag.

The antiseptic is introduced into application bag 910 through fill/drain port 140, solution deployment pouch 220, or plastic rectangle 352. The exterior of the application bag is then manipulated to assure coverage of the appendage by the antiseptic fluid. The antiseptic fluid is then rubbed or massaged into the skin through application bag 910 to dislodge biological communities. Scrub brush 900 and/or application bag 910 is manipulated to scrub the skin to dislodge bacterial colonies. Excess antiseptic fluid is retained by application bag 910. Since application bag 910 is transparent or substantially transparent, a visual examination of the extremity is conducted to assure that adequate and complete coverage of the surgical site has been made.

Upon removal of application bag 910, care must be taken to ensure that any portion of the non-sterile exterior of application bag 910 does not come into contact with the now sterile extremity of the patient. To accomplish removal without contact, gasket 120, closing means 230, or elastic band 720 is rolled back so that only its sterile interior is adjacent the extremity. Application bag 910 is then removed by sliding it off of the extremity, making sure that the rolled back edge is the only point of contact.

Referring then to FIG. 11E, an alternate embodiment of a scrub brush will be described.

Brush assembly 959 comprises of docking fixture 960 and brush 966. Docking fixture 960 in a preferred embodiment is HDPE plastic approximately three by four inches in size and one quarter inch in thickness. Docking fixture 960 includes adhesive surface 970, adapted to be permanently fixed to the interior surface of an application bag. Docking fixture 960 includes dovetail slot 962. Dovetail slot 962 is adapted to mate with dovetail peg 964 of brush 966. Brush 966 is also, in a preferred embodiment, comprised of HDPE plastic. Brush 966 includes bristles 975 permanently fixed to its bottom surface.

Figure 11A:
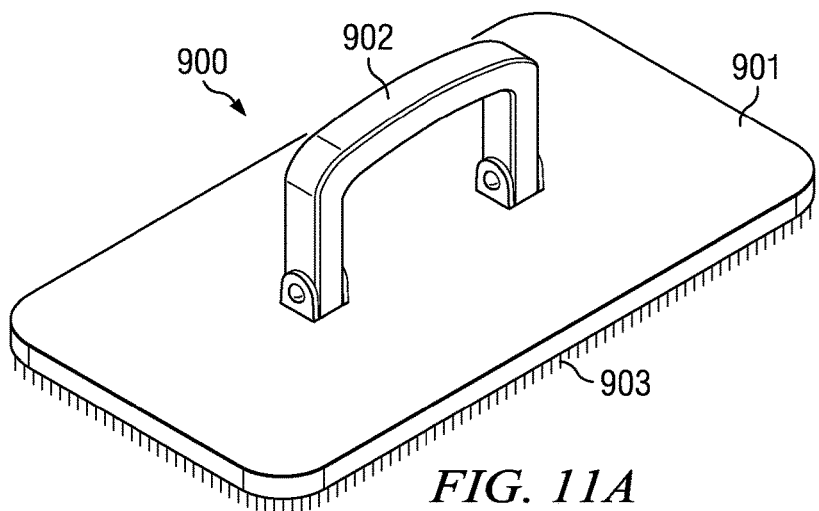
FIG. 11A is a perspective view of a scrub brush of a preferred embodiment of the invention.
Figure 11B:
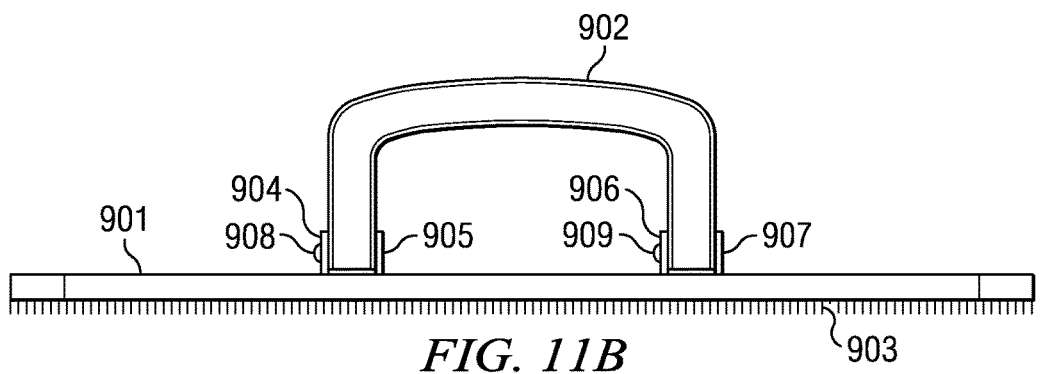
FIG. 11B is a side view of a scrub brush of a preferred embodiment of the invention.
Figure 11C:
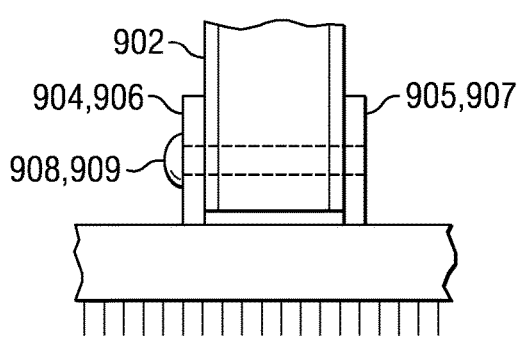
FIG. 11C is a detail view of a connection means of a scrub brush of a preferred embodiment of the invention.
Figure 11D:
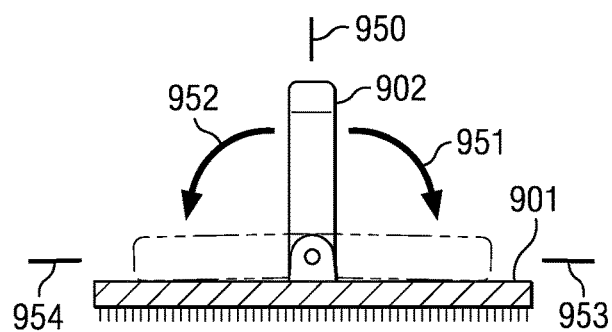
FIG. 11D is an end view of a scrub brush of a preferred embodiment of the invention.
Figure 11F:
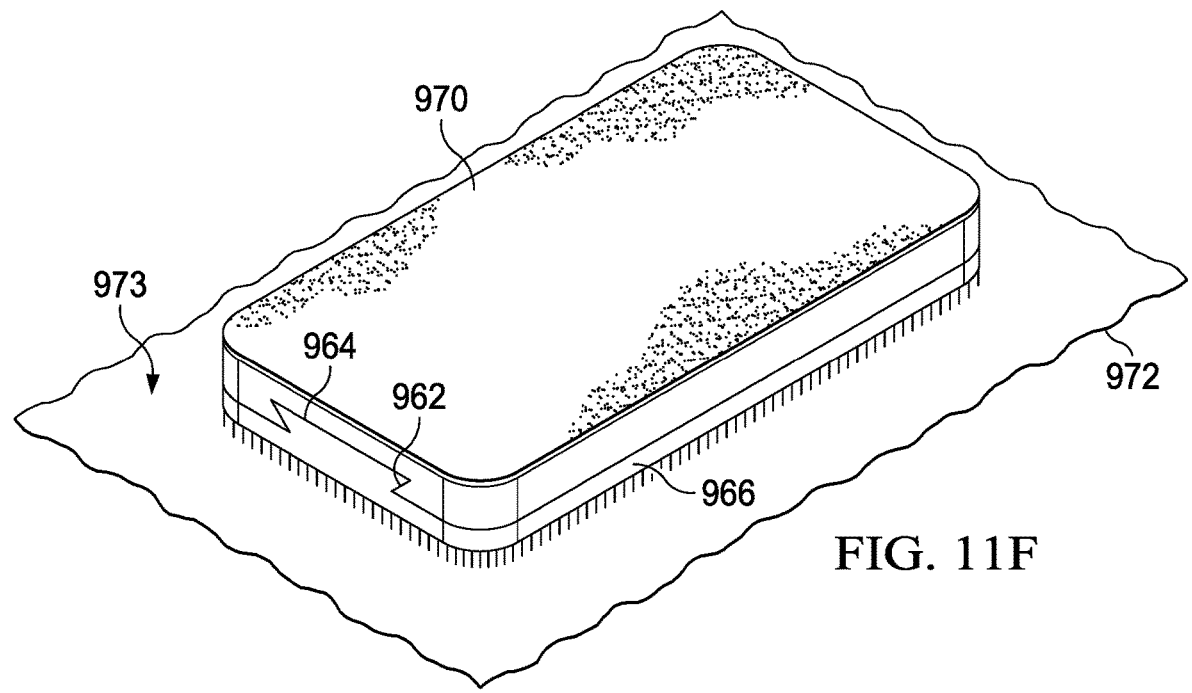
FIG. 11F is a perspective view of a preferred embodiment of a scrub brush secured in a docking fixture attached to an application bag.

Referring to FIG. 11F, as can be seen adhesive surface 970 is permanently affixed to interior surface 972 of application bag 973. It can also be seen that brush 966 is nested in docking fixture 960 through the mating of dovetail slot 962 with dovetail peg 964.

In use, brush assembly 959 is affixed to the interior surface of an application bag when application bag is deployed. After the application bag is applied to the patient, the brush assembly is disassembled by removing brush 966 from docking fixture 960 for use inside the application bag.

Figure 11G:
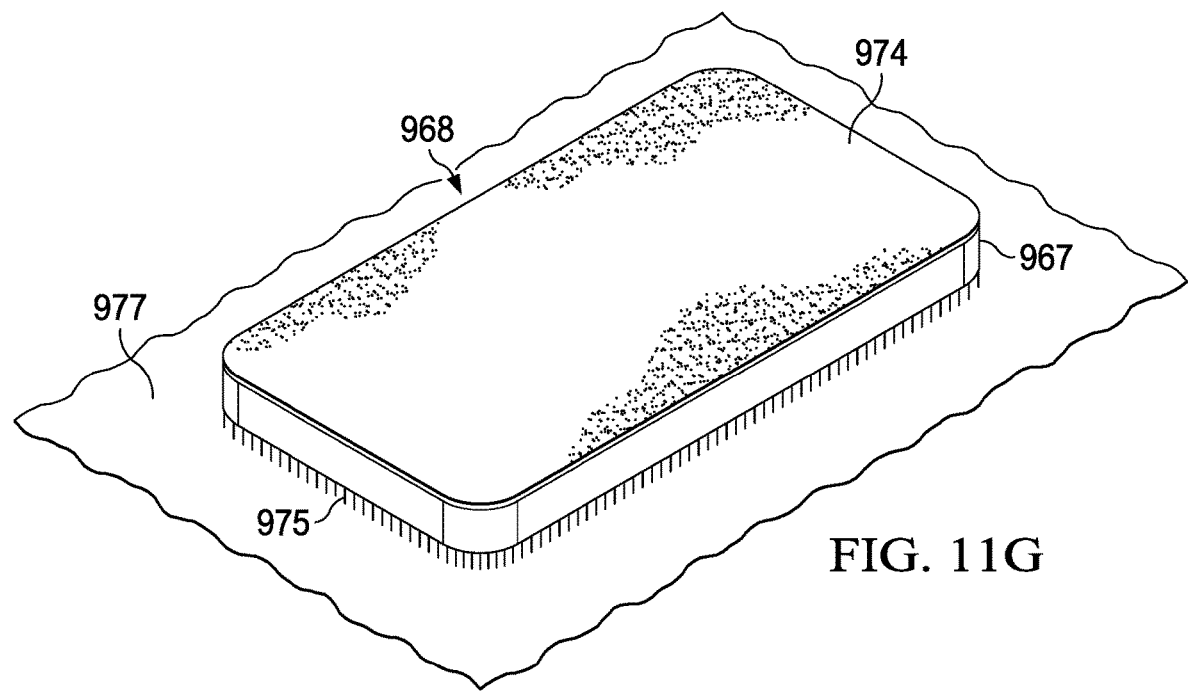
FIG. 11G is a perspective view of a scrub brush removably secured to an application bag.

Referring then to FIG. 11G, an alternate embodiment of a scrub brush will be described. Scrub brush 968 include brush body 967. Brush body 967 is preferably comprised of an HDPE plastic. Brush body 967 includes permanently affixed bristles 975 for use in cleaning or debridement procedures.

Brush body 967 further includes adhesive surface 974. In a preferred embodiment, adhesive surface 974 includes an aggressive yet removable adhesive such as available from 3M. In a preferred embodiment, the adhesive surface is affixed to the interior surface of application bag 977 when the application bag is deployed.

After deployment, the application bag is affixed to the patient and the brush body may be removed from the interior surface of the application bag for use.

Figure 12A:
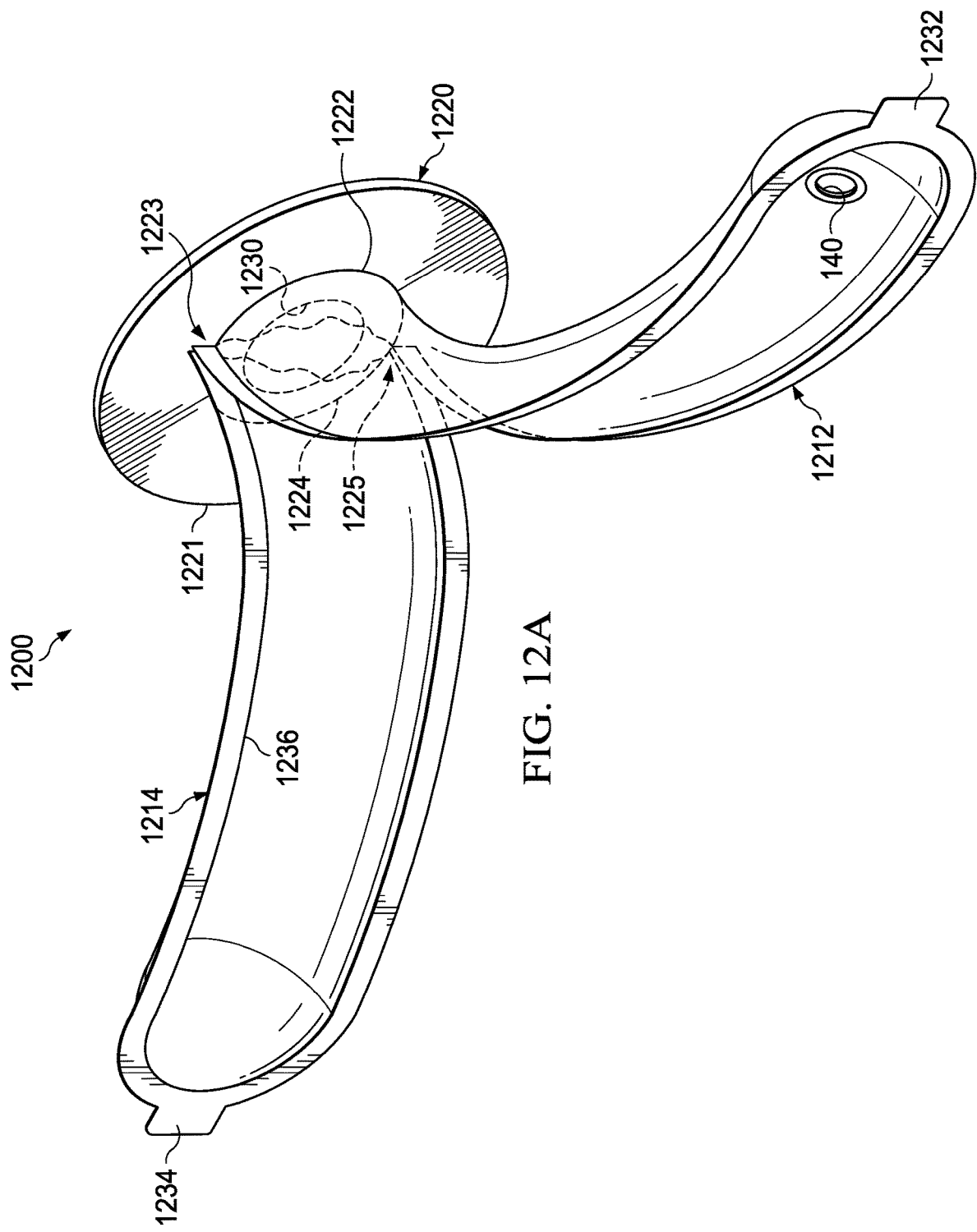
FIG. 12A is a perspective view of a preferred embodiment showing two resealable halves separated.
Figure 12B:
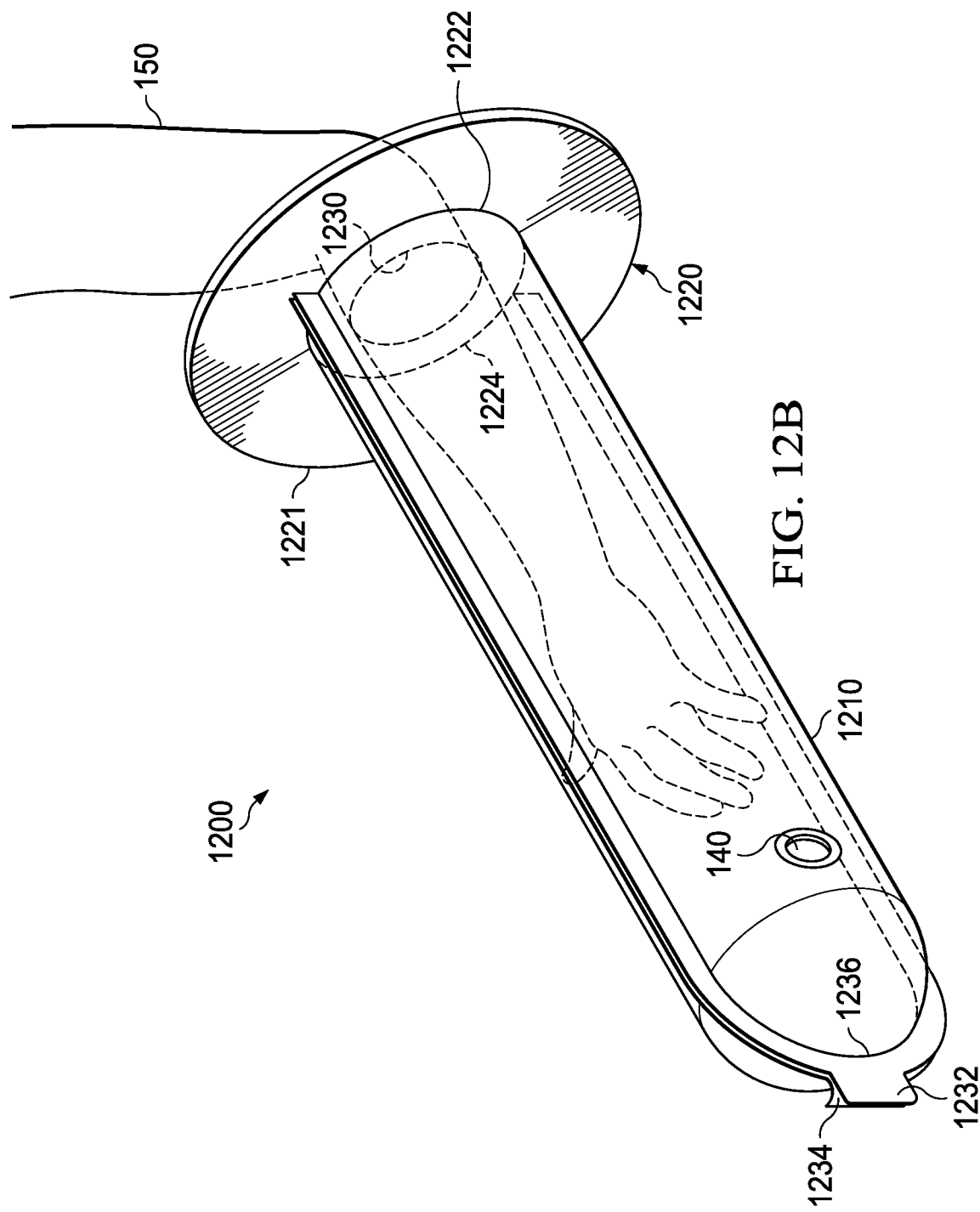
FIG. 12B is a perspective view of a preferred embodiment showing two resealable halves joined.
Figure 12C:
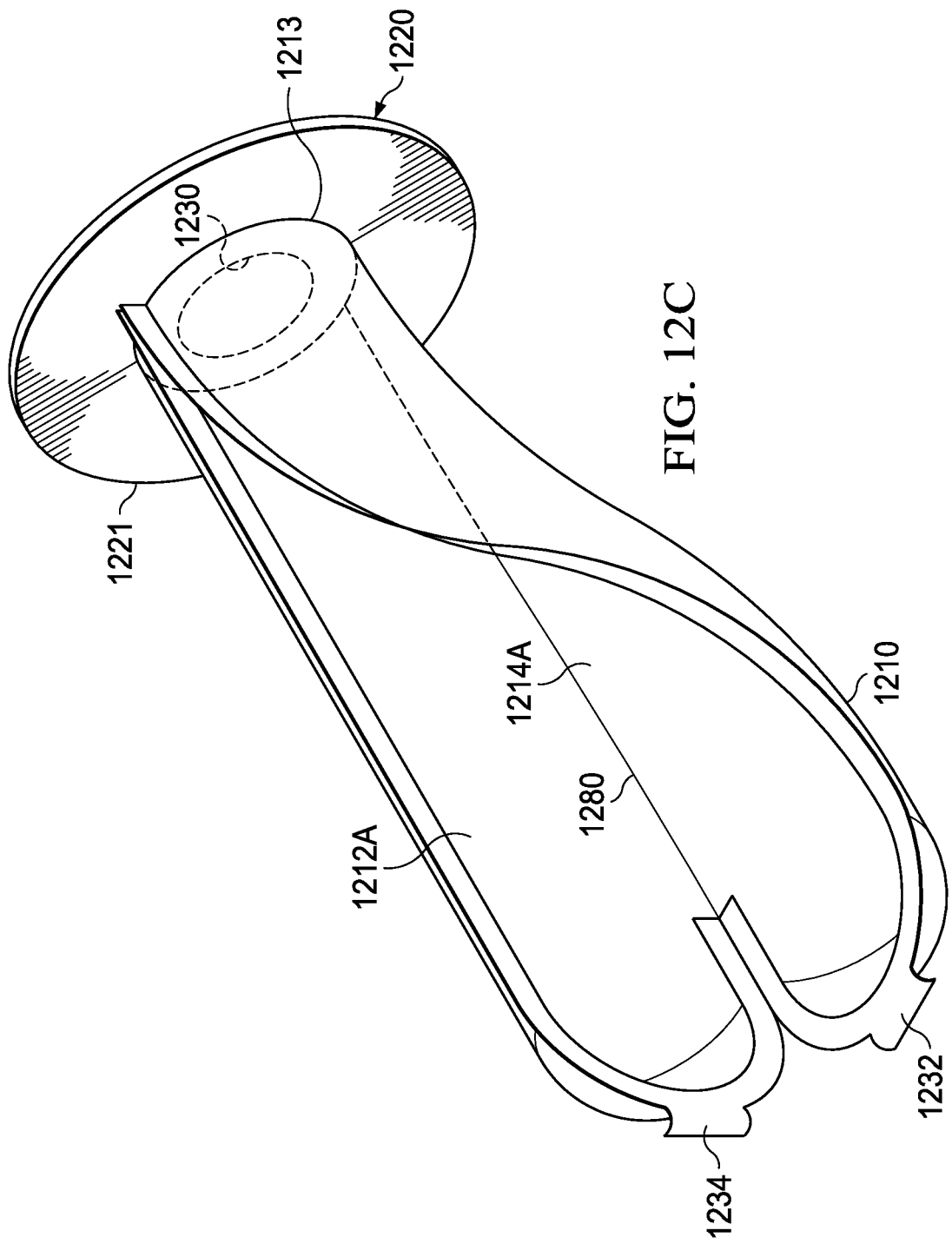
FIG. 12C is a perspective view of a preferred embodiment of two resealable halves with a fold line.

FIGS. 12A and 12B show a preferred embodiment of solution applicator 1200. Solution applicator 1200 comprises two releasably joinable halves connected to a flexible gasket. Solution applicator 1200 is comprised of first portion 1212 and second portion 1214. First portion 1212 and second portion 1214 may be equally sized separate halves. Alternatively, first portion 1212a and second portion 1214a may be formed from a single sheet folded at fold line 1280 as shown in FIG. 12C. An end of first portion 1212 and an end of second portion 1214 are each fused or sealed to gasket 1220 through a known adhesive, tape, or heat welding to ensure a sealed attachment. First portion 1212 is attached to gasket 1220 at attachment area 1222 and second portion 1214 is attached to gasket 1220 at attachment area 1224. The shape of the attachment areas are generally semicircular, but other shapes are possible. Attachment areas 1222 and 1224 converge at points 1223 and 1225 thus a complete seal to gasket 1220 is achieved. The attachment areas can be formed through inductive heat welding or a suitable flexible adhesive. First portion 1212 includes tab 1232 and second portion 1214 includes tab 1234.

Gasket 1220 can be manufactured from synthetic rubber, such as neoprene or nitrile, or a resilient plastic polymer. The gasket color can be coded to indicate the size and/or shape of the bag making for easy and error free deployment of the antiseptic solution.

Gasket 1220 is generally flat and circular shaped, however oval and polygonal shapes would suffice. Gasket 1220 has perimeter edge 1221 along the perimeter of gasket 1220 and hole 1230 generally in the center of gasket 1220. In a preferred embodiment, the diameter of hole 1230 ranges between about 1 inch and 15 inches. However, those skilled in the art will recognize that other sizes can be provided to accommodate different patients and circumstances. Hole 1230 should fit around a body extremity such as to prevent the antiseptic solution from escaping application bag 1210 when in use. In this embodiment, there is a single circumferential attachment area 1213 located between hole 1230 and perimeter edge 1221.

Attached to first portion 1212, second portion 1214, or both is fastening means 1236. Fastening means 1236 releasably attaches first portion 1212 to second portion 1214 to form application bag 1210. Fastening means 1236 can be any releasable fastening means that is "watertight" such that the antiseptic introduced into application bag 1210 remains inside application bag 1210 when the first portion is fastened to the second portion. Fastening means 1236 can include, but is not limited to, releasable adhesive or a plastic zipper similar to Ziplock®.

Application bag 1210 can include a multitude of antiseptic insertion means including one of, but not limited to, the aforementioned fill/drain port 140, solution pouch 220 including cavity 305 and capsule 330, and plastic rectangle 352. Additionally, instead of gasket 1220, application bag 1210 may incorporate elastic band 720 or closing means 230 with hook section 260 and receiver section 250. The interior and/or exterior surfaces of application bag 1210 may be textured and/or include a brush or other high friction scrubber.

Referring to FIGS. 12D and 12E, application bag 1250 is comprised of an expanded opening 1262 bounded by split gasket 1256 and adhesive closure 1257. The material of the application bag may comprise a rough texture to facilitate scrubbing the extremity as previously described. Split gasket 1256 is comprised of a synthetic rubber such as neoprene or nytril, but also can be formed from resilient plastic polymer coated with a suitable aggressive adhesive for direct application to the exterior of an appendage or extremity. Expanded opening 1262 is important because it provides an opening suitable for large wounds or immobilized limbs which will not otherwise fit through a smaller opening.

Application bag 1250 may also further comprise various embodiments of brush 1266 and frangible capsule 1268 fixed to its interior, as previously described.

Adhesive closure 1257 further comprises first section 1258 and second section 1260. First section 1258 and second section 1260 are sealed together at joint 1264 by inductive welding or a suitable adhesive. In a preferred embodiment the inside surface of both first section 1258 and second section 1260 is coated with a suitably aggressive yet releasable adhesive which allows for a resealable closure between the two, as shown in FIG. 12D. In a preferred embodiment, the adhesive can be obtained from 3M Corporation as Part No. 1509. In an alternate embodiment, first section 1258 and second section 1260 comprise a "zip-lock" type zipper closure. Both first section 1258 and second section 1260 can be joined to application bag 1250 through heat welding or other suitable sealing adhesive. In another preferred embodiment, first section 1258 and second section 1260 may be integrally formed with the application bag.

In an alternate embodiment, the interior of split gasket 1256 and the interior of first section 1258 and second section 1260 of adhesive closure of 1257 are covered by a waxed cover strip 1270, shown in FIG. 12E. In this way, the application bag may be shipped and deployed without exposing the adhesive surfaces of the gasket or the adhesive closure to contaminants before use. The cover strip(s) may be removed, thereby exposing the adhesive closure(s). After removal, the cover strip is discarded. The cover strip feature may be used with any of the embodiments described which comprise an adhesive strip closure. Then the interior surfaces of first section 1258 and second section 1260 are sealed by use of the adhesive on the interior surfaces.

Application bag 1250 further includes flap 1275. Flap 1275 includes adhesive strip 1276 around its perimeter. Flap 1275 is positioned adjacent hole 1278. Hole 1278 is surrounded by adhesive strip 1277. Flap 1275 is integrally formed with the application bag along fold line 1279. In use, flap 1275 may be closed thereby joining adhesive strip 1276 with adhesive strip 1277 and forming a seal between the flap of the application bag. The flap may be opened by releasing adhesive strip 1276 from adhesive strip 1277 thereby exposing hole 1278. Hole 1278 leads directly to the interior of the application bag and may be used to access the patient during cleaning procedures.

In a preferred embodiment, adhesive strips 1276 and 1277 is a suitable non-aggressive adhesive which allows for repeated separation. In an alternate embodiment, flap 1275 may include a "zip-lock" releasable plastic seal in place of the adhesive strips.

Application bag 1250 further comprises access port 1252 and access port 1254 as will be further described.

Figure 13A:
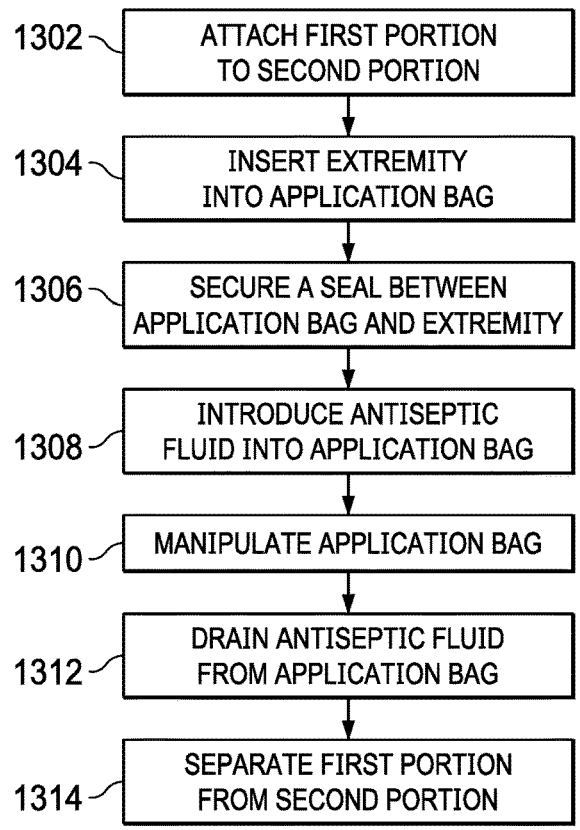
FIG. 13A is a flowchart of the steps involved in the use of certain preferred embodiments.

Referring now to FIG. 13A, the steps for a preferred use of the various embodiments of FIGS. 12A, 12B and 12C of the application bag are shown. At step 1302, first portion 1212 is joined to second portion 1214 with fastening means 1236. In this step, the waxed cover strips are removed exposing the adhesive closures. Fastening means 1236 provides a watertight seal. At step 1304, appendage 150 is inserted into application bag 1210 through hole 1230 in gasket 1220. Steps 1302 and 1304 may be reversed in sequence. In other words, the appendage may be inserted through hole 1230 after fastening first portion 1212 to second portion 1214 or first portion 1212 may be fastened to second portion 1214 after appendage 150 passes through hole 1230. At step 1306, gasket 1220 secures a seal between application bag 1210 and appendage 150.

Once first portion 1212 is fastened to second portion 1214, at step 1308, antiseptic fluid is introduced to the interior of application bag 1210 through fill/drain port 140, solution deployment pouch 220, or plastic rectangle 352. At step 1310, application bag 1210 is manipulated to apply the antiseptic fluid to the appendage and to dislodge bacterial colonies.

After disinfecting the appendage with the antiseptic fluid, at step 1312, the excess antiseptic fluid is drained through fill/drain port 140 or by separating the first portion from the second portion without disturbing the appendage. At step 1314, if not previously separated, first portion 1212 is separated from second portion 1214. To separate the first portion from the second portion, tab 1232 is peeled away from tab 1234 such that first portion 1212 is unfastened from second portion 1214. With the appendage disinfected and exposed, gasket 1220 may remain in place while physicians move forward with surgery on the appendage. Post surgery, application bag 1210 may be reassembled to protect the surgical site from bacteria before transferring the patient from the surgical environment to the recovery area. One of skill in the art will recognize that these steps may also be applied to other embodiments of the application bag as required.

Figure 13B:
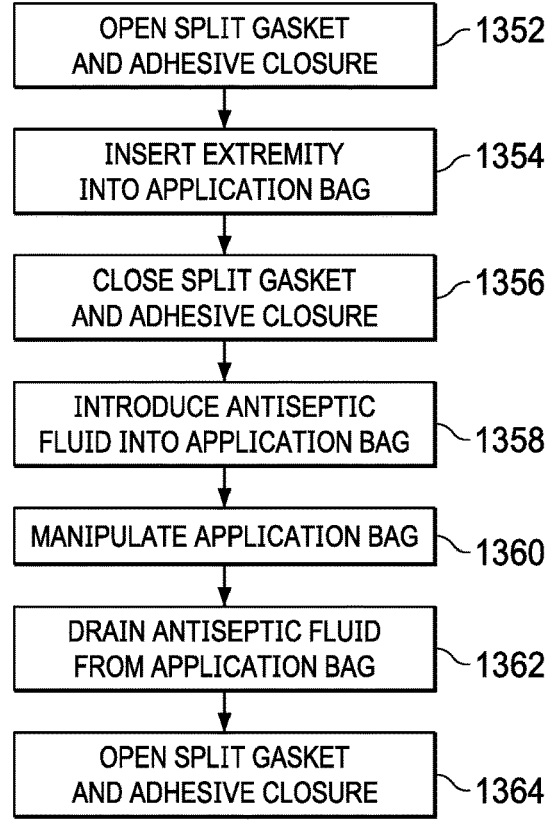
FIG. 13B is a flowchart of the steps involved in use of certain preferred embodiments.

Referring now to FIG. 13B, a preferred use of the various embodiments of FIGS. 12D and 12E of the application bag are shown. At step 1352, the expanded opening is opened by opening split gasket 1256 and adhesive closure 1257. In a preferred embodiment, the application bag is presented for initial use with a waxed cover strip that covers adhesive surfaces of the split gasket and the adhesive closure. In another embodiment, the adhesive closure includes a "ziplock" type connection which is opened before use.

At step 1354, an appendage is inserted into the application bag through split gasket 1256 and adhesive closure 1257. At step 1356, the split gasket and the adhesive closure are joined to provide a water tight seal between the interior of the application bag and the exterior of the application bag. In this step, the waxed cover strip is removed before the adhesive surfaces are joined together.

At step 1358, antiseptic fluid is introduced into the interior of the application bag through either or both of access port 1252 and/or access port 1254. In another preferred embodiment, antiseptic fluid is introduced into the interior application bag through hole 1278. Antiseptic may also be introduced through frangible capsule 1268.

At step 1360, the application bag is manipulated to apply the antiseptic fluid to the appendage and dislodge bacterial colonies. If present, brush 1266 may be used to remove bacterial colonies. At step 1362, the excess antiseptic fluid is drained through any of access port 1252, access port 1254 or hole 1278. At step 1364, the split gasket and the adhesive closure are opened to expose the disinfected appendage for surgery. One skill in the art will recognize that these steps may also be applied to other embodiments of the application bag as required.

Figure 14A:
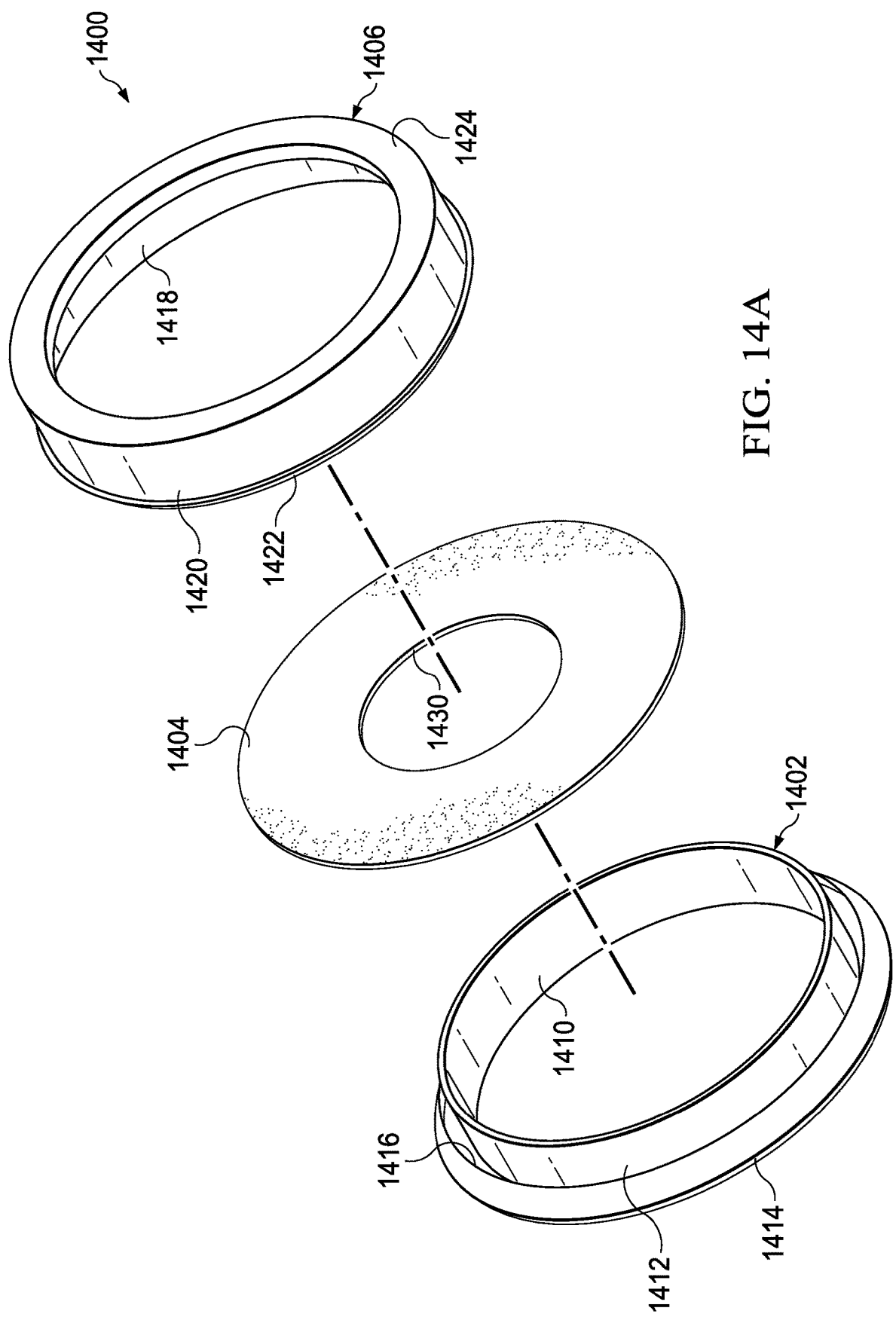
FIG. 14A is an exploded perspective view of an alternate sealing means of a preferred embodiment.
Figure 14B:
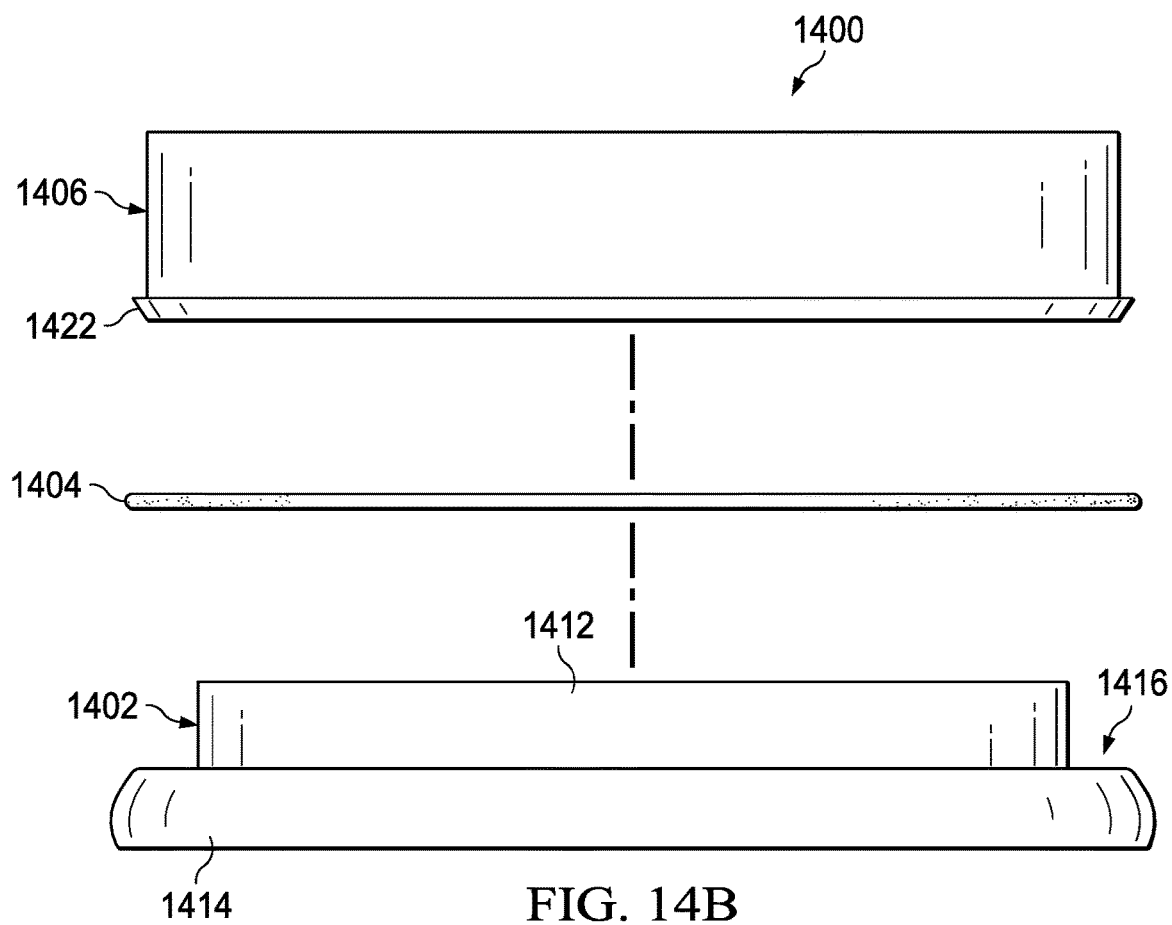
FIG. 14B is an exploded side view of an alternate sealing means of a preferred embodiment.
Figure 14C:
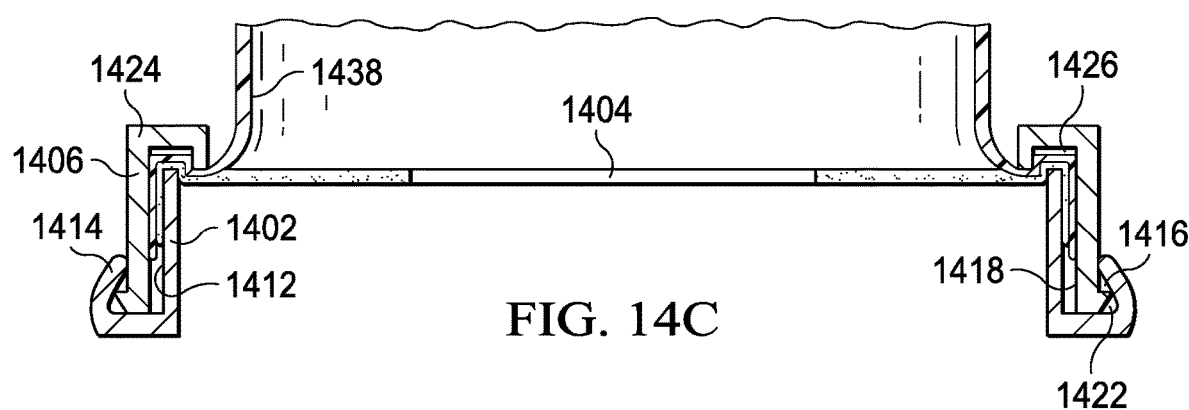
FIG. 14C is a sectional side view of an alternate sealing means of a preferred embodiment.

Referring now to FIGS. 14A, 14B and 14C, sealing means 1400 is shown. Sealing means 1400 comprises inner ring 1402, gasket 1404, and outer ring 1406. Those skilled in the art will recognize that sealing means 1400 can be used in conjunction with any of the previously disclosed solution applicators to ensure a sealed attachment of an application bag to a gasket.

Inner ring 1402 is a cylinder having inner surface 1410 and outer surface 1412. Outer surface 1412 includes lip 1414 around the exterior perimeter. Lip 1414 forms channel 1416.

Outer ring 1406 is a cylinder having inner surface 1418 and outer surface 1420. Outer surface 1420 includes tab 1422 around the exterior perimeter. Tab 1422 is sized to engage channel 1416. Inner surface 1418 includes lip 1424 around the interior perimeter. Lip 1424 forms channel 1426. Channel 1426 is sized to conform to inner ring 1402. The diameters of inner ring 1402 and outer ring 1406 range between 5 inches and 20 inches. However, those skilled in the art will recognize that other sizes can be provided to accommodate different patients and procedures. Inner ring 1402 and outer ring 1406 are manufactured of commercially available flexible plastic, including but not limited to polypropylene, polyethylene, or polystyrene.

Gasket 1404 is generally flat and circular. Other shapes would suffice. In a preferred embodiment, diameter of gasket 1404 ranges between 6 inches and 24 inches. Hole 1430 is positioned in the relative center of gasket 1404. In a preferred embodiment, diameter of hole 1430 ranges between about 1 inch and 15 inches. However, those skilled in the art will recognize that other sizes can be provided to accommodate different patients and procedures. Hole 1430 should fit around a body extremity such as to prevent the antiseptic solution from escaping the application bag incorporating sealing means 1400. Gasket 1404 can be manufactured from synthetic rubber, such as neoprene or nitrile, or a resilient plastic polymer.

As best shown in FIG. 14C, the diameter of inner ring 1402 is smaller than the diameter of outer ring 1406 to allow inner ring 1402 to nest snuggly within outer ring 1406. Gasket 1404 and application bag 1438 are constrained between outer surface 1412 and inner surface 1418. The gasket and the application bag conform to channel 1426 as inner ring 1402 is pressed into channel 1426. In an alternate embodiment, the application bag may further extend such that it is constrained within channel 1416 by tab 1422 and lip 1414.

Referring to FIGS. 14C and 15, application bag 1438 attached to gasket 1404 with sealing means 1400 will be described. To attach the application bag to the gasket, gasket 1404 is positioned adjacent inner ring 1402 such that gasket 1404 covers inner ring 1402. An open end of the application bag surrounds gasket 1404 and inner ring 1402. The opposite end of the application bag is inserted through outer ring 1406 and outer ring 1406 is nested with inner ring 1402. The open end of application bag 1438 and gasket 1404 is held in position within channel 1426 by inner ring 1402 as inner ring 1402 is nested within outer ring 1406. Sealing means 1400 creates a watertight seal between application bag 1438 and gasket 1404 so that antiseptic introduced is contained within application bag 1438. Gasket 1404 of sealing means 1400 secures a seal between application bag 1438 and appendage 1450 as appendage 1450 extends through hole 1430.

Those skilled in the art will recognize that a more complete application of antiseptic fluid can be made due to the fact that application takes place outside the operating theater. Those skilled in the art will also recognize that the antiseptic can be retained on the surgical area longer, promoting a more thorough decontamination. Those skilled in the art will also recognize that since the decontamination can take place outside the operating theater that substantial operating theater time can be saved with resulting monetary savings to the patient and the hospital.

A bacterial load comparison of standard operating room disinfection techniques versus use of a surgical preparation solution applicator bag for preparing a patient's skin for surgery prior to entering the surgical theater as disclosed herein was performed. A summary of the results are presented here.

The bacterial load comparison utilized a standard skin-swabbing followed by inoculation and agar plating approach to quantify the bacterial load before and after disinfection. In total, 60 skin-swab samples were collected for processing and 27 were used for final analysis.

For collection of swabbing, a single person served as their own control. Per person, left and right arms were swabbed individually and collected in tubes. Then one arm was disinfected with standard operating room disinfection techniques while the other arm was disinfected using the disclosed surgical preparation solution application bag. Both arms were then individually swabbed again and collected in individual tubes resulting in four samples per person.

Samples were plated without dilution on three Petri dishes containing Brain-heart infusion agar (Difco) supplemented by defibrinated horse blood (BAP-medium), thus providing a triplicate count per sample. The plates were incubated at 30° C. and the resulting colonies were counted at 48 hours and 72 hours post-platting. This specific Petri dish medium was selected because it supports the growth of most common skin bacteria and particularly those bacteria that can cause wound infections (e.g., enterics, *Staphylococcus* and *Streptococcus* spp., *Pseudomonas aeruginosa*).

Following colony counting, six samples were removed from further consideration due to spreading fungal growth. The presence of fungi on the Petri dishes does not necessarily indicate contamination from sampling or plating. Fungi may have been present on the skin of sampled individuals. The medium used in the study was designed for counting bacteria, specifically because (1) bacterial count was the focus of the study and (2) bacteria are expected to be the main component of skin microflora. Moreover, counting of fungal colonies was not possible due to the exceedingly fast growth rate of fungal colonies on the medium. The study did not attempt to quantify fungal load and accordingly samples displaying fungal growth were excluded from the study.

Other samples contained no bacterial growth or on average less than one bacterium per Petri dish replicate. For these samples, both left and right arms and three replicates from each arm produced identical numbers (i.e., a lack of bacterial growth) suggesting that a lack of bacteria is not associated with sampling or plating errors but rather the lack of a culturable bacterial load on the skin of these subjects.

Additional samples yielded one or more Petri dishes with confluent colonies and were assigned with "too numerous to count" designation. The number of plated bacteria for these samples exceeded 1,000 which is considered an upper limit of colonies that can be counted on one standard Petri dish. Accordingly, the twenty seven remaining samples with two to three replicates each were selected for further statistical analyses.

Qualitatively, both disinfection techniques performed superbly by removing almost all bacteria in the samples. For the standard technique, an average number of colonies recovered was 0.05 per plate. For the surgical preparation solution applicator bag disclosed herein, the average number of colonies recovered was 0.012 colonies per plate. A paired t-test was used to compare the number of colonies grown in a Petri dish from samples collected after the sterilant treatment of an individual to the number of colonies grown in a control Petri dish from the same individual.

The resulting $t(78$ degrees of freedom$)=1.778172$ and $p=0.039636$. Thus, the result is significant at $p<0.05$. When $p<0.05$, "the magnitude of the effect" becomes of interest. The observed mean difference of $8.67\pm4.88$ suggests that on average the disclosed surgical preparation solution applicator bag killed 8.67 more bacteria/per plate in this study than the standard disinfection techniques. Although, the mean difference can be explained by a systematic sampling error, the paired t-test demonstrates that the surgical preparation solution applicator bag disclosed herein is at least as good as the standard disinfection techniques commonly used in the operating theater.

In summary, the surgical preparation solution application bag disclosed herein demonstrated the efficiency of disinfection not worse than and possibly better than that of standard techniques, essentially killing all bacteria on sampled skin areas.

Figure 16A:
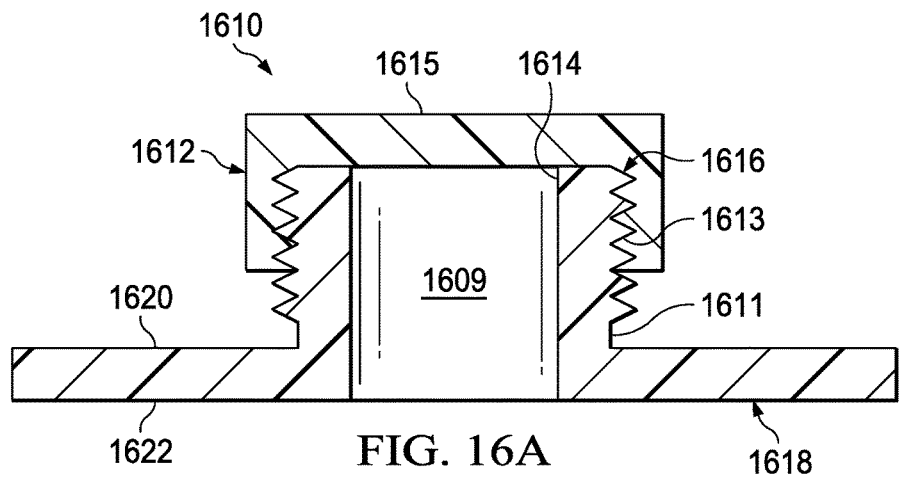
FIG. 16A is a sectional side view of an alternative port connector of a preferred embodiment.
Figure 16B:
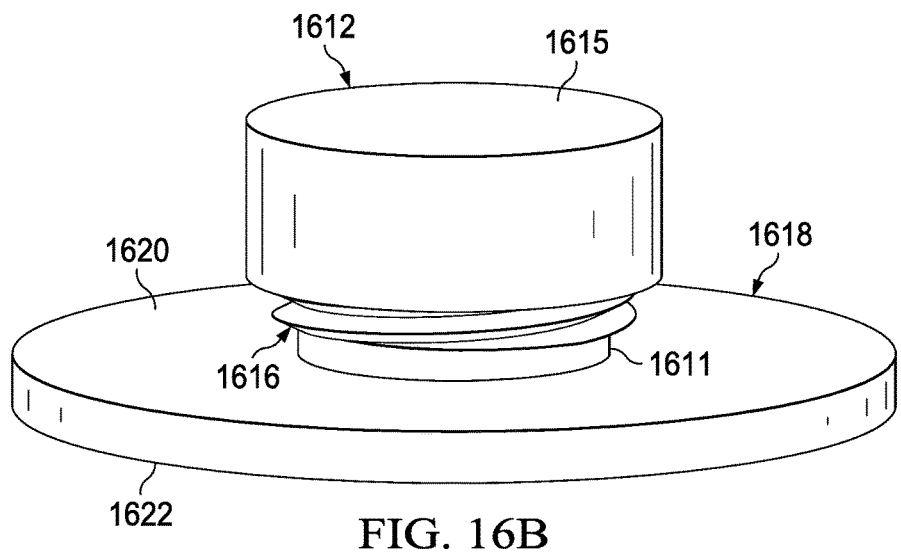
FIG. 16B is a perspective view of an alternative port connector of a preferred embodiment.

Referring now to FIGS. 16A and 16B, port connector 1610 will be further described. Port connector 1610 comprises connection ring 1618 and cap 1612.

Connection ring 1618 includes vertical stanchion 1611, outer surface 1620 and inner surface 1622. Vertical stanchion 1611 proceeds generally perpendicularly to outer surface 1620. Together outer surface 1620 and inner surface 1622 form a circular disk. Inner surface 1622 comprises hole 1609 in inner surface 1614. Vertical stanchion 1611 further comprises threaded section 1616. In alternate embodiments, either outer surface 1620 or inner surface 1622 may be adapted to be sealed by heat welding to the application bag such that hole 1609 is ductedly connected to the interior of the application bag through a corresponding hole (not shown) in the application bag. A suitable adhesive can also be employed to bond either outer surface 1620 or inner surface 1622 to the application bag.

Cap 1612 generally comprises threaded section 1613 and top 1615. Threaded section 1616 is adapted to mate with threaded section 1613. The figure shows the threads on the outside of the vertical stanchion and on the inside of the top. However, in another embodiment the threads may be on the inside of the vertical stanchion and on the outside of the top, as shown in FIG. 1B. In either case, when cap 1612 and connection ring 1618 are engaged, a seal exists between the cap and vertical stanchion 1611. Thereby preventing escape of fluids from the application bag through hole 1609.

Figure 16C:
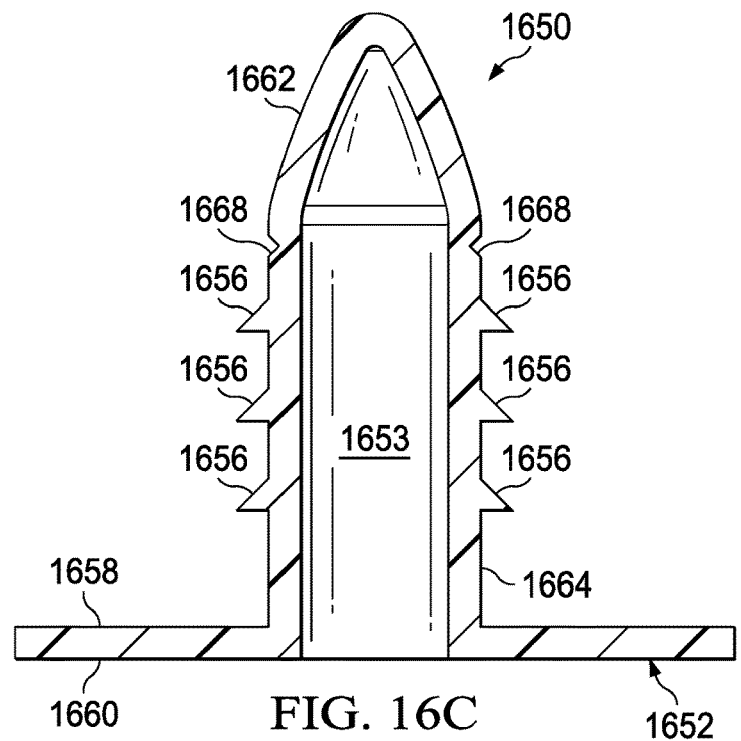
FIG. 16C is a cross-sectional view of an alternative port connector of a preferred embodiment.
Figure 16D:
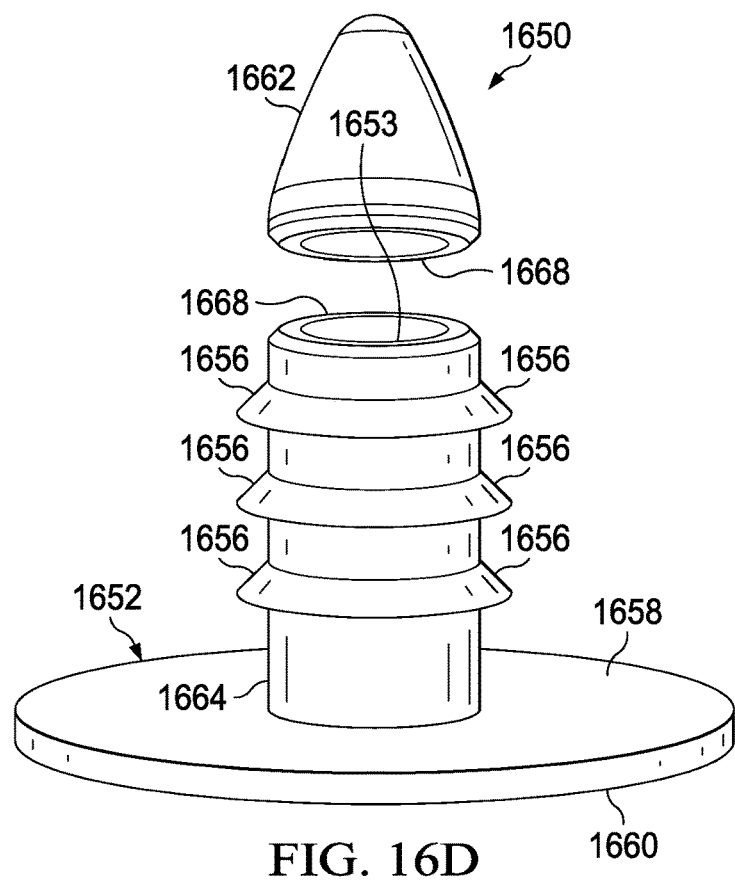
FIG. 16D is an exploded perspective view of an alternative port connector of a preferred embodiment.

Referring then for FIGS. 16C and 16D an alternative embodiment of a port connector will be described. Port connector 1650 is generally comprised of connection ring 1652 and vertical stanchion 1664. Vertical stanchion 1664 proceeds generally perpendicularly from connection ring 1652. Connection ring 1652 further comprises outer surface 1658 and inner surface 1660. Together outer surface 1658 and inner surface 1660 form a flat disk. Either outer surface 1658 or inner surface 1660 is adapted to be heat welded to the application bag or affixed with a suitable permanent adhesive, such that hole 1653 is ductedly connected to the interior of the application bag. Vertical stanchion 1664 further comprises a plurality of resistance rings 1656. In a preferred embodiment, each resistance ring forms a frustoconical surface on the exterior of vertical stanchion 1664. At the distal end of vertical stanchion 1664, nipple 1662 is integrally formed with vertical stanchion 1664. As shown in FIG. 16C nipple 1662 is adapted to be removed from vertical stanchion 1664 by cutting.

In a preferred embodiment, port connector 1650 is comprised of nytril rubber or neoprene. In another preferred embodiment, port connector 1650 is comprised of frangible polypropylene. In this embodiment, nipple 1662 may be broken from vertical stanchion 1664 along indented break line 1668.

Vertical stanchion 1664 and resistance rings 1656 are adapted to fit the interior surface of a flexible tube (not shown) as will be further described. The resistance rings securely attach the flexible tube to the connector and prevent leakage. In use, port connector 1650 is adapted to be used as an exhaust port for the application bag when nipple 1662 is broken from vertical stanchion 1664 and a flexible tube attached.

Figure 16E:
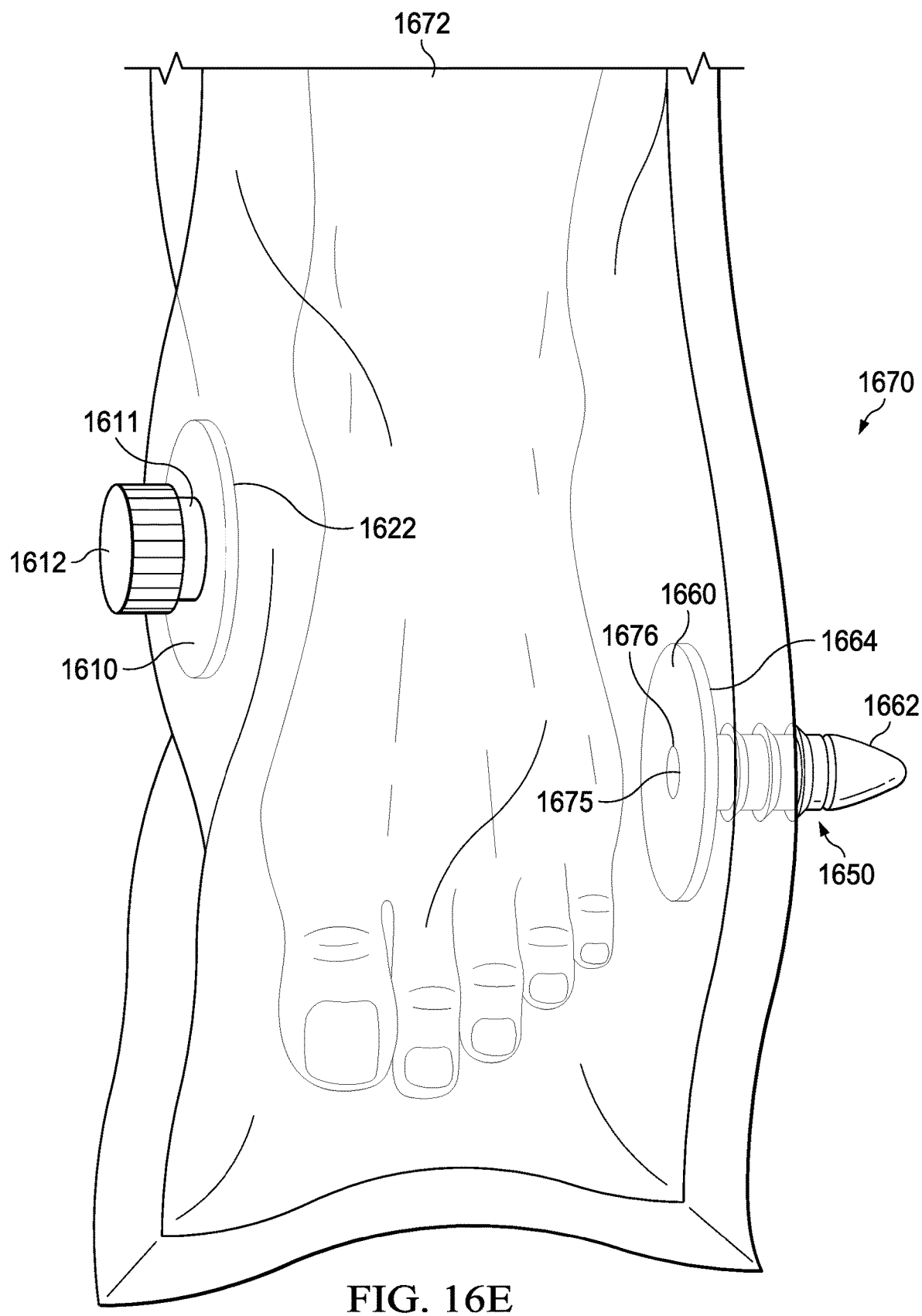
FIG. 16E is a plan view of an alternative embodiment of the application bag including two port connectors.

Referring to FIG. 16E, application bag 1670 includes port connector 1610 and port connector 1650 affixed to an exterior surface. Any of the port connectors previously described may suffice. As can be seen, in this embodiment, inner surface 1622 of port connector 1610 is sealingly affixed to the exterior of application bag 1670. A hole in the application bag (not shown) resides adjacent the hole in the port connector. In like manner, inner surface 1660 of port connector 1650 is sealingly affixed to the exterior surface of application bag 1670. Hole 1675 in the application bag is positioned adjacent hole 1676 in the port connector. In this embodiment, port connector 1610 and port connector 1650 are arranged on opposite sides of application bag 1670.

In use, cap 1612 is removed from vertical stanchion 1611 for the introduction of antiseptic fluid or other instrumentality into application bag 1670 for treatment of appendage 1672. Optionally cap 1612 may be replaced after treatment. In use, nipple 1662 is cut from vertical stanchion 1664 to allow for connection of a drain tube onto port connector 1650. The drain tube allows for the exhaust and disposal of antiseptic fluid after treatment. As can be seen, inner surface 1660 is sealingly affixed to an exterior surface of application bag 1670. Those skilled in the art will observe that if nipple 1662 is not removed from vertical stanchion 1664, that port connector 1650 remains sealed and so does not allow the escape of treatment fluids. The optional removal of nipple 1662 is important because it allows the treatment provider to decide whether or not to enable drainage. This can be important in emergency situations where drainage not required at triage, but is further required upon arrival at a medical facility.

Figure 17:
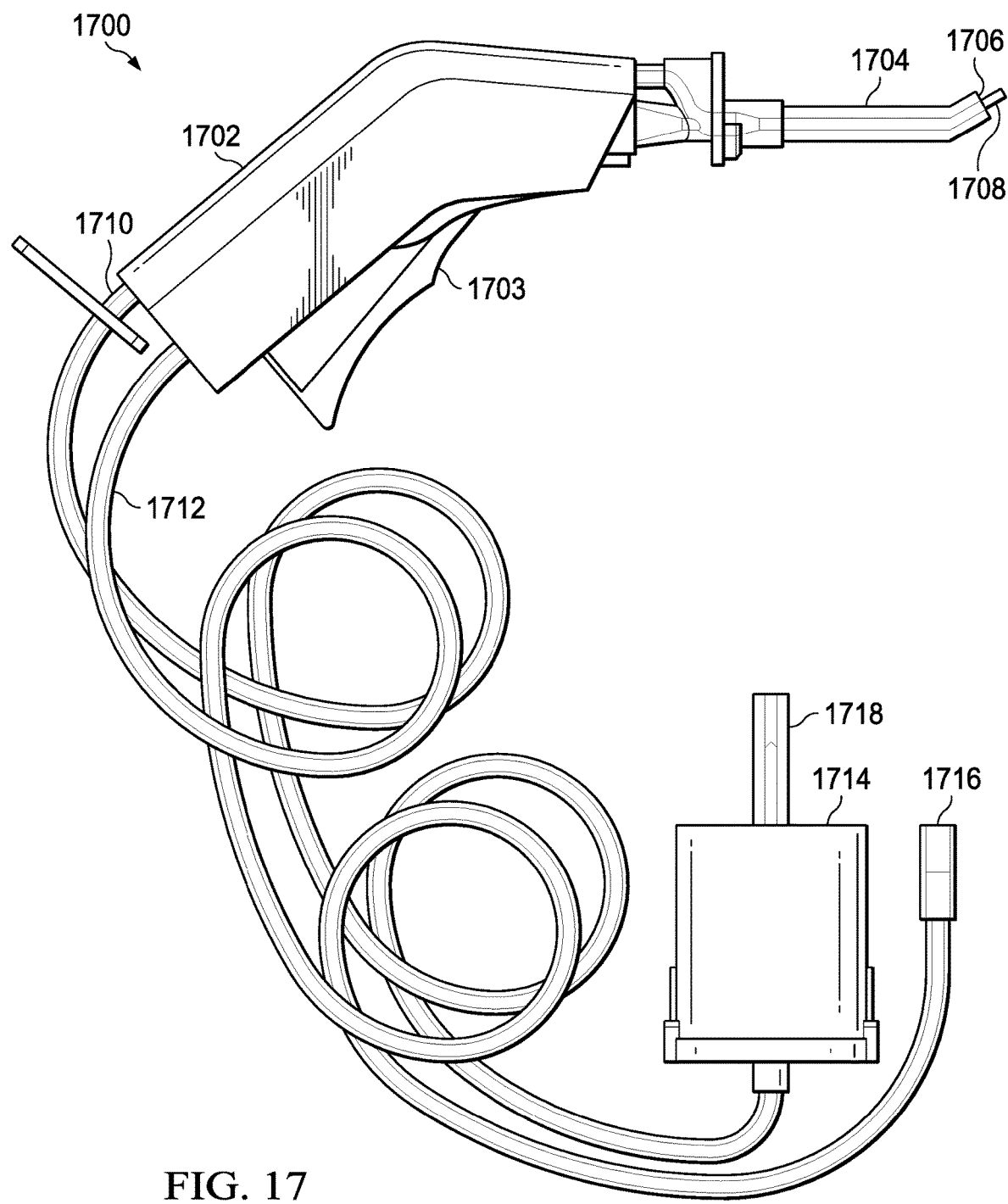
FIG. 17 is a perspective view of a pulse lavage system for use with a preferred embodiment.

Referring then to FIG. 17, lavage system 1700 will be described. Lavage system 1700 comprises of hand piece 1702 connected to fluid supply line 1710 and suction line 1712. Hand piece 1702 further comprises trigger 1703 and barrel 1704. Barrel 1704 further comprises suction tip 1706 and lavage tip 1708. Lavage tip 1708 is ductedly connected to fluid supply line 1710 through a pump (not shown) internal to hand piece 1702. Suction tip 1706 is ductedly connected to suction line 1712 through hand piece 1702.

Fluid supply line 1710 is connected to fluid supply connector 1718. Adjacent fluid supply connector 1718 is power supply 1714. Power supply 1714 is operatively connected to the pump in hand piece 1702 and supplies power for its operation when trigger 1703 is depressed. Suction connector 1716 is connected to suction line 1712.

When in use, lavage system 1700 is connected to a supply of suction and exhaust via suction connector 1716. Fluid supply connector 1718 is connected to a fluid supply such as saline or other antiseptic or antibiotic fluids. In operation, trigger 1703 is depressed activating the pump internal to hand piece 1702 thereby drawing fluid through the fluid supply line and discharging it through lavage tip 1708 at high pressure. Negative pressure from the suction connector 1716, and suction line 1712 is communicated to suction tip 1706 which attracts and exhausts the spent fluid dispensed from lavage tip 1708.

Figure 18A:
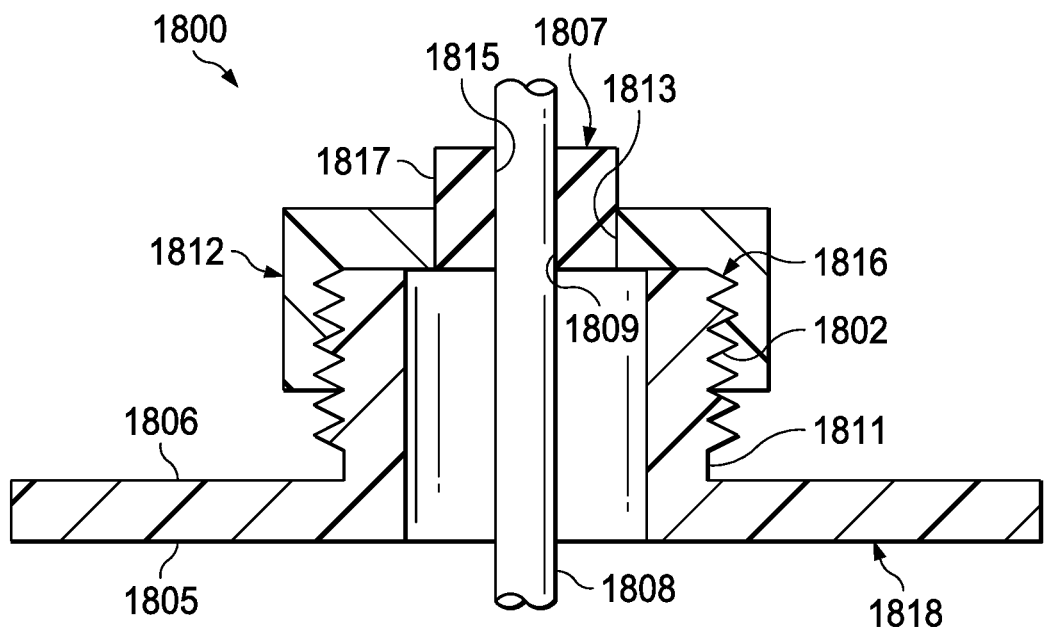
FIG. 18A is a cross-sectional view of an alternative port connector of a preferred embodiment.
Figure 18B:
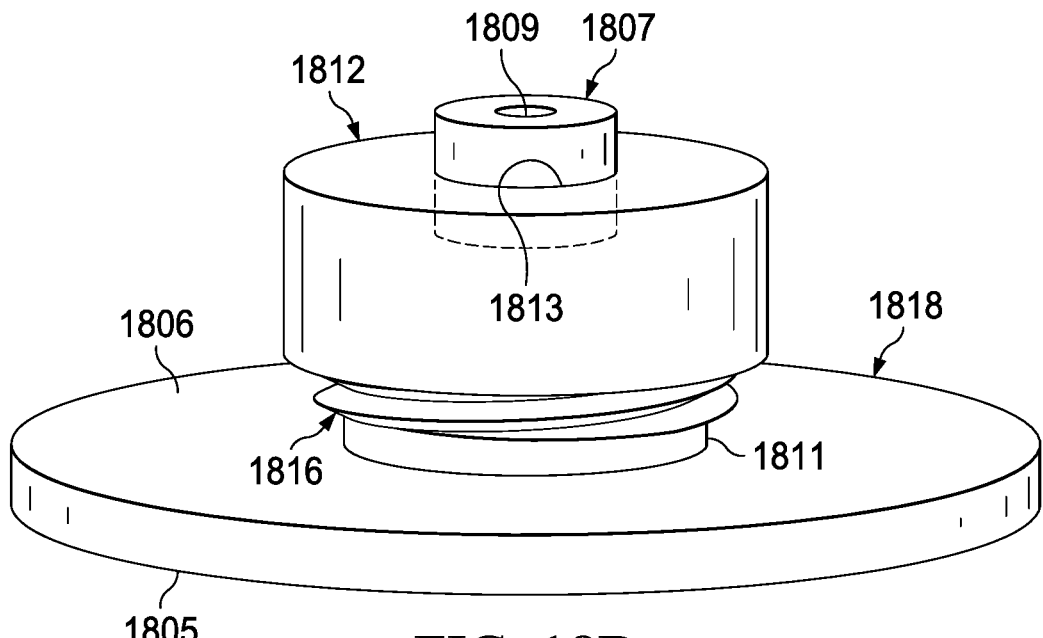
FIG. 18B is a perspective view of an alternative port connector of a preferred embodiment.

Referring then to FIGS. 18A and 18B an preferred embodiment of port connector 1800 will be described. Port connector 1800 is comprised of connection ring 1818 including vertical stanchion 1811. The connection ring includes inner surface 1805 and outer surface 1806, and is adapted to be sealed to an application bag as previously described. Vertical stanchion 1811 includes threaded section 1816.

Port connector 1800 further comprises of cap 1812 including threads 1802. Threads 1802 are adapted to mate with threaded section 1816. Cap 1812 further includes hole 1813. Bushing 1807 is fitted within hole 1813. In a preferred embodiment, bushing 1807 is sealed against hole 1809 and prevents fluid leakage between the two. Bushing 1807 is preferably made of a flexible neoprene or butyl rubber. Bushing 1807 includes inner section 1815, outer section 1817 and hole 1809. Inner section 1815 is adapted to seal against barrel 1808 of a lavage system, yet allow rotation between the barrel and the inner surface, such that fluid transfer between the two is not possible. As can be seen, bushing 1807 enables barrel 1808 to be turned about its axis with respect to port connector 1800 without rotational movement of connection ring 1818.

Figure 18C:
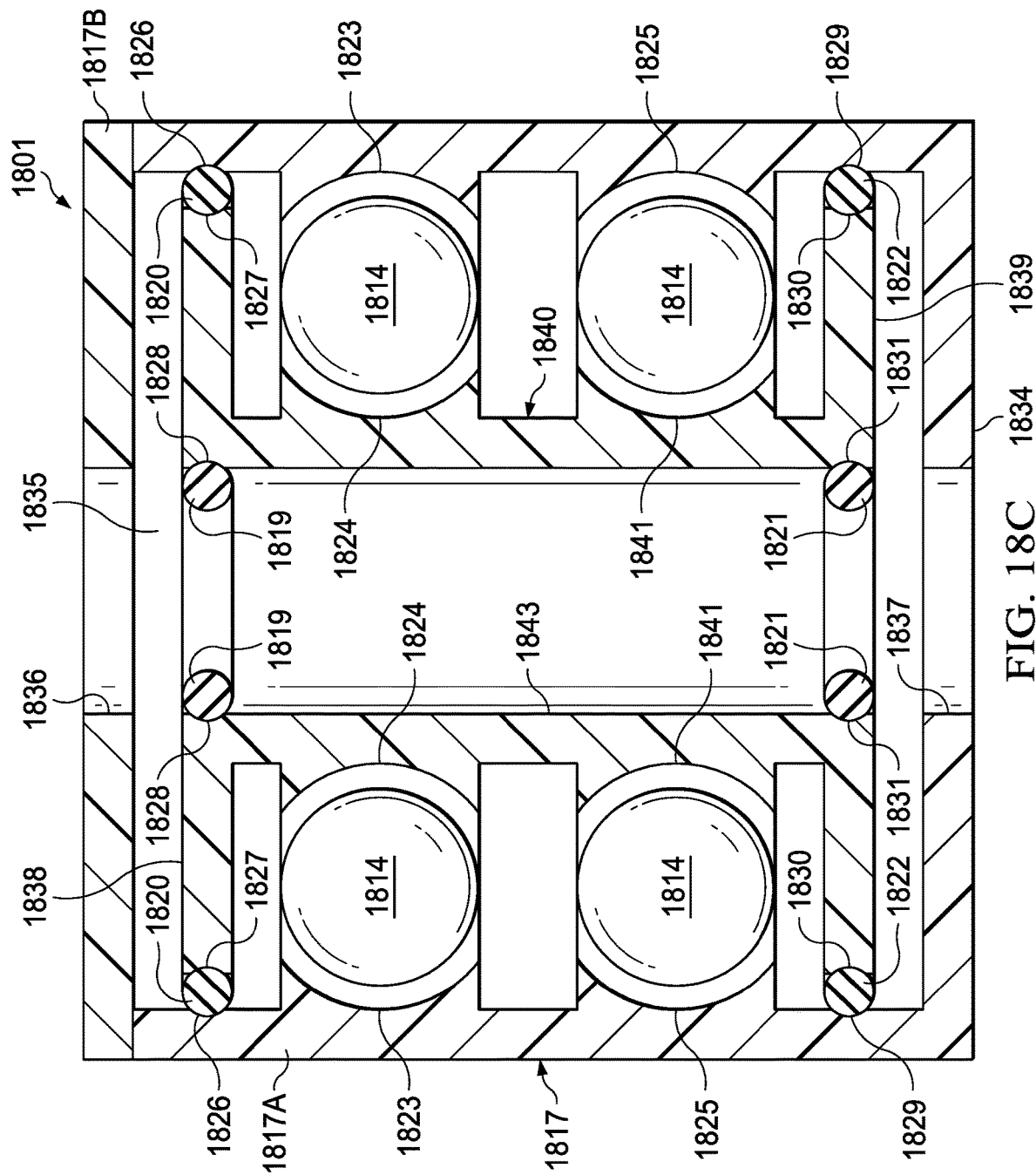
FIG. 18C is a cross-sectional view of a rotary coupling of a preferred embodiment.
Figure 18D:
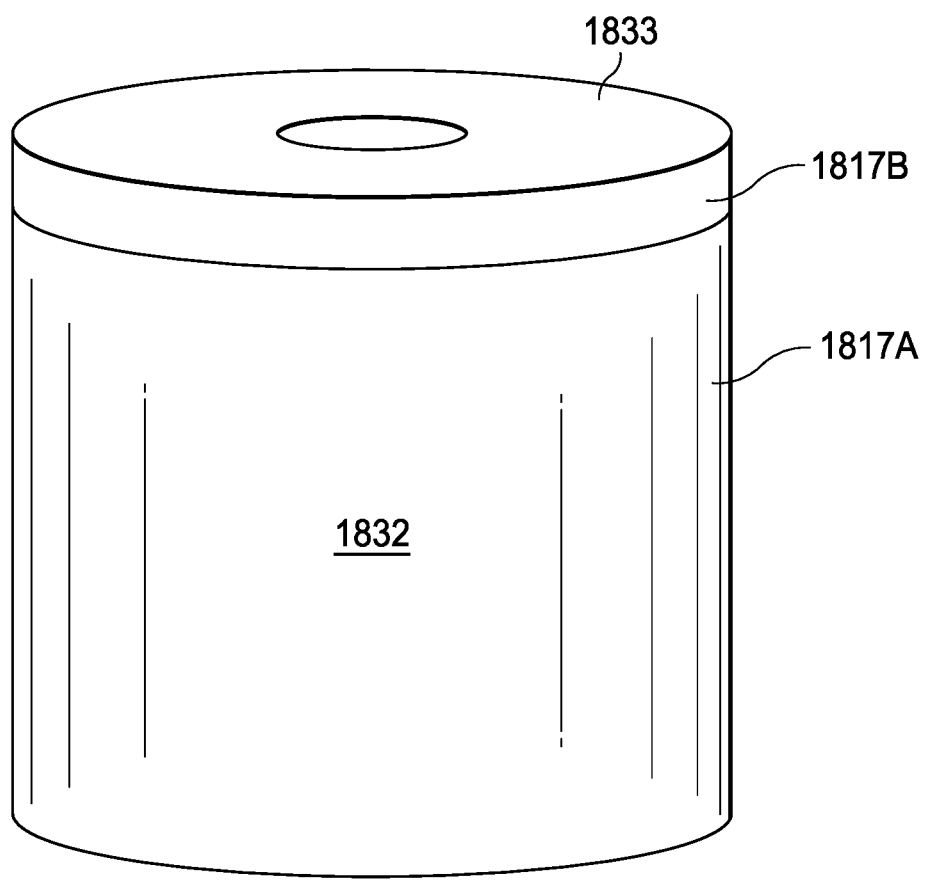
FIG. 18D is a perspective view of a rotary coupling of a preferred embodiment.

Referring then FIGS. 18C and 18D, an alternative embodiment of the rotary coupling will be described. Rotary coupling 1801 generally comprises outer section 1817 and inner section 1840. Outer section 1817 is generally cylindrical and is comprised of lower section 1817a and upper section 1817b. The two sections are joined together by mating threads (not shown) or by a suitable permanent adhesive such as epoxy. When the lower section and the upper section are assembled, they comprise top surface 1833, exterior surface 1832 and bottom surface 1834. The top surface, exterior surface and bottom surface generally form cavity 1835. Within cavity 1835, the outer section includes seal seat 1826 and seal seat 1829. Further within cavity 1835, outer section 1817 includes bearing race 1823 and bearing race 1825. Fitted within seal seat 1826 is sealing ring 1820. Fitted within seal seat 1829 is sealing ring 1822. In a preferred embodiment, the sealing rings are neoprene o-rings.

Bearings 1814 are fitted within bearing races 1823 and 1825 and are sized to rotate within them.

Top surface 1833 further includes hole 1836. Likewise bottom surface 1834 includes hole 1837.

Inner section 1840 is a generally cylindrical spool including top surface 1838, interior surface 1843 and bottom surface 1839. Inner section 1840 is nested within cavity 1835. Top surface 1838 includes seat 1827 and seat 1828. Sealing ring 1820 is fitted within seat 1827. Sealing ring 1819 is fitted within seat 1828. Bottom surface 1839 includes seat 1830 and seat 1831. Sealing ring 1822 is fitted within seat 1830. Sealing ring 1821 is fitted within seat 1831. In a preferred embodiment, the sealing rings are neoprene O-rings. Interior surface 1843 includes bearing race 1824 and bearing race 1841. Bearings 1814 are operatively disposed within bearing races 1824 and 1841.

In use, a barrel of the lavage system (not shown) is fitted into and sealed against sealing rings 1819 and 1821 preventing fluid passage between them. As the barrel is rotated about its axis, inner section 1840 rotates within cavity 1835 of outer section 1817, enabled by bearings 1814 rolling within the bearing races. Fluid conduction through hole 1837 is prevented by the seal between sealing ring 1821, sealing ring 1819 and the barrel. Rotation of the barrel within hole 1837 is important because it allows rotational positioning of the lavage head without wrinkling or constriction of the application bag to enable greater access to the wound for wound treatment.

Figure 18F:
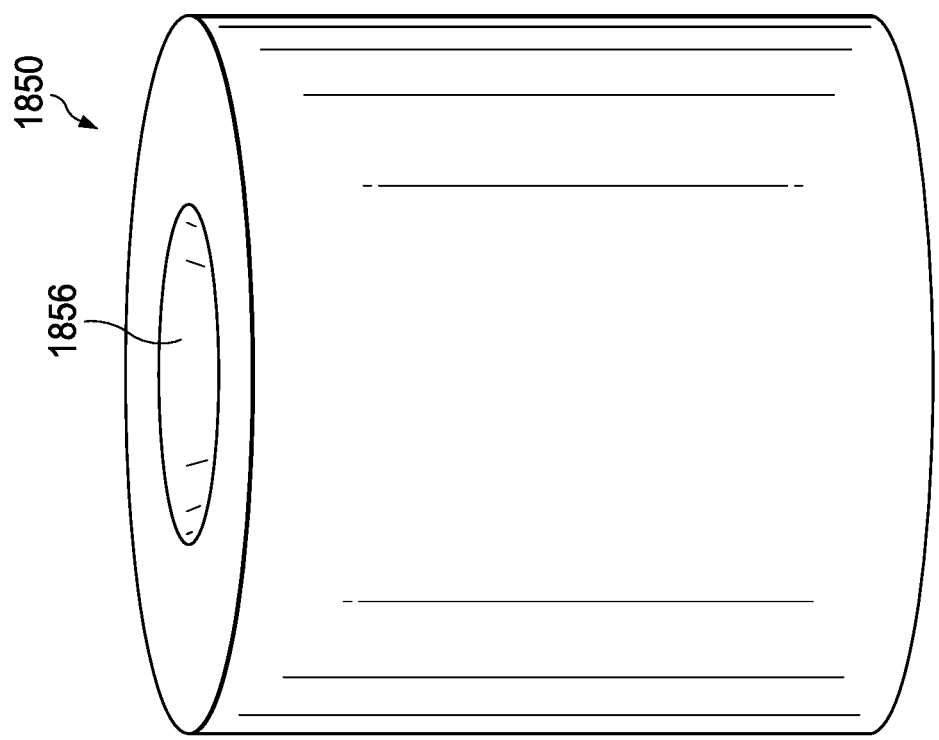
FIG. 18F is a perspective view of an angled coupling of a preferred embodiment.
Figure 18E:
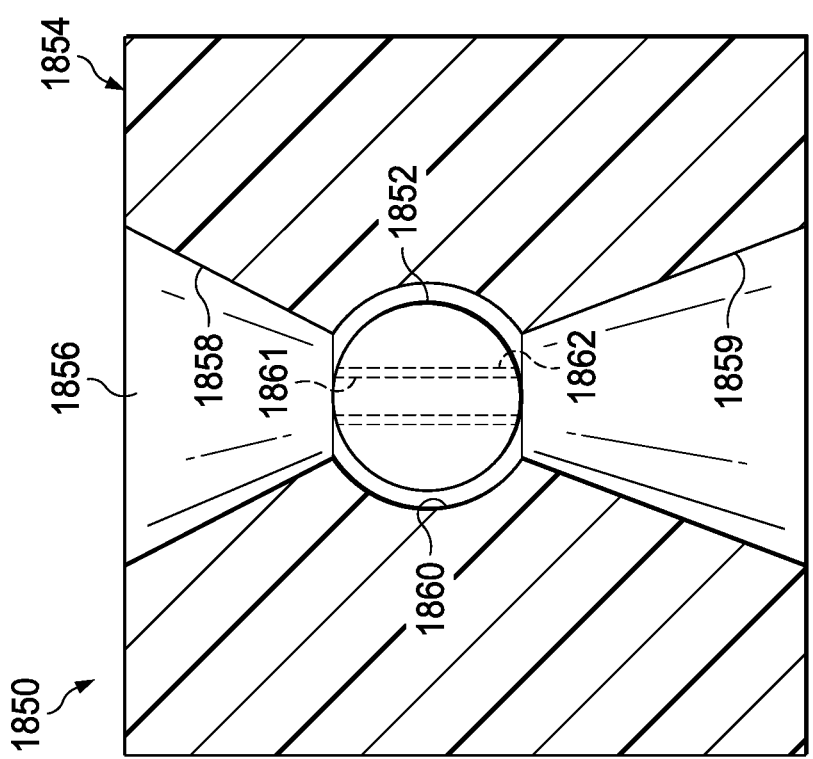
FIG. 18E is a cross-sectional view of an angled coupling of a preferred embodiment.

Referring then to FIGS. 18E and 18F a preferred embodiment of an angled coupling will be described.

Angled coupling 1850 is comprised gimble body 1854 and gimble 1852. Gimble body 1854 includes hole 1856. Hole 1856 includes upper frustoconical section 1858, lower frustoconical section 1859 and spherical section 1860. Gimble 1852 is spherical and sized to be sealingly fitted within spherical section 1860. The tolerance between gimble 1852 and spherical section 1860 is such that rotation with three degrees of freedom is allowed between the two. Gimble body 1854 is preferably constructed of a bioinert plastic such as Teflon or Dalrin. Similarly, gimble 1852 is comprised of Teflon or Dalrin. A suitable silicon grease is deployed between spherical section 1860 and gimble 1852 to reduce friction.

Gimble 1852 further comprises hole 1861. Cylindrical seal 1862 is fitted within hole 1861. Cylindrical seal 1862 is affixed to gimble 1852 within hole 1861 by a suitable bioinert adhesive.

In use, a barrel of a lavage system is fitted within hole 1861 adjacent cylindrical seal 1862. Cylindrical seal 1862 prevents fluid transfer between lower frustoconical section 1859 and upper frustoconical section 1858. Likewise, fluid transfer is prevented between spherical section 1860 and gimble 1852.

Figure 18G:
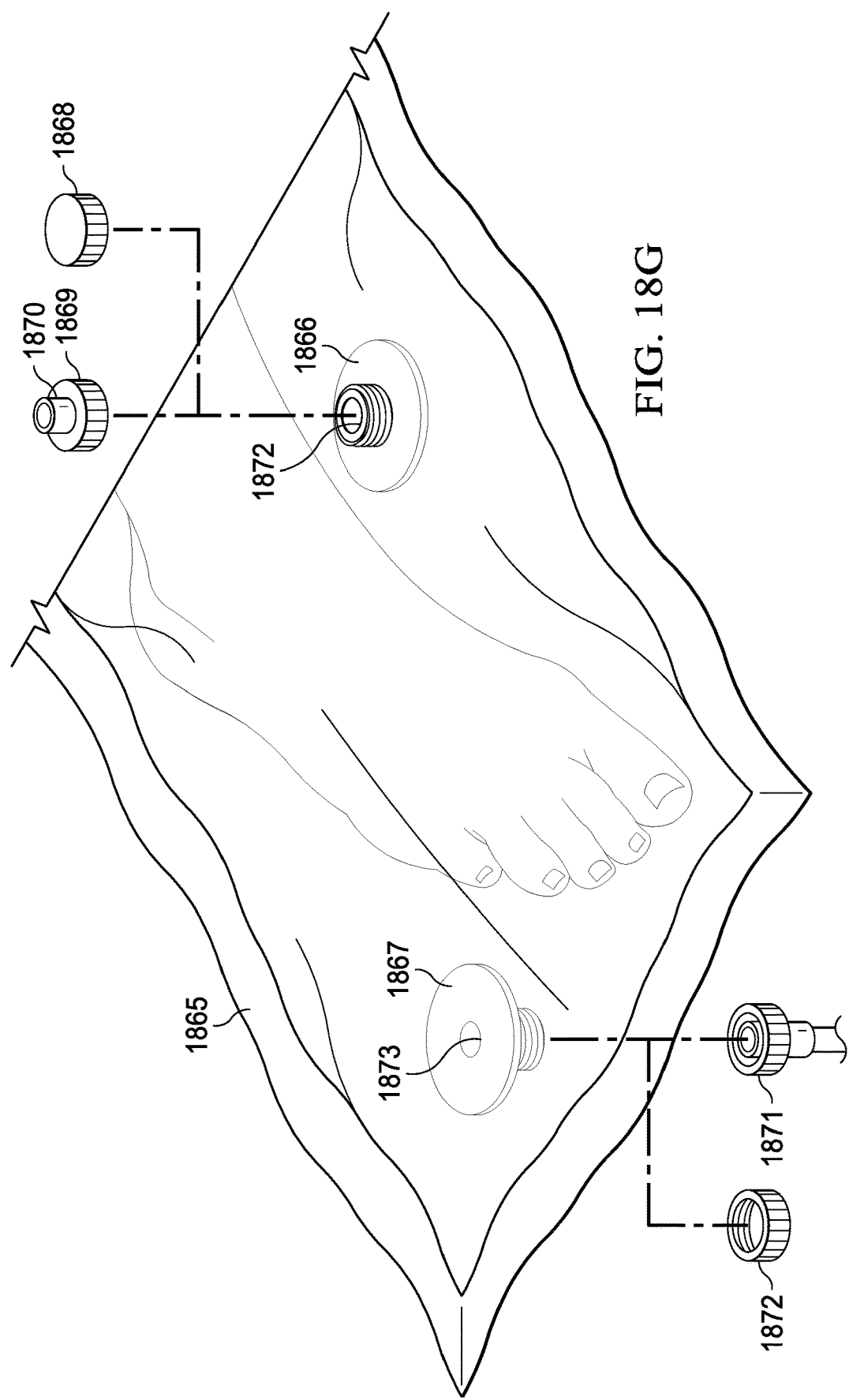
FIG. 18G is an exploded view of a preferred embodiment including two port connectors.

Referring then to FIG. 18G, an alternate embodiment of the application bag will be described.

Application bag 1865 is affixed to port connector 1866 and port connector 1867. The inner surface of each port connector is secured to the exterior of the application bag by a suitable adhesive. Port connectors 1866 and 1867 are held in ducted communication with the interior of the application bag through hole 1872 and hole 1873, respectively.

Port connector 1866 may be fitted alternatively with cap 1868 or cap 1869. As an example, cap 1869 may include rotary connector 1870.

Cap 1868 is used to seal port connector 1866. Cap 1869 is used to allow entry of a lavage system through rotary connector 1870.

Port connector 1867 is fitted alternatively with cap 1872 and drain connector 1871. Drain connector 1871 is further connected to a collection bag, which will be further described. Cap 1872 is used to seal port connector 1867 with respect to the interior of application bag 1865.

Figure 19A:
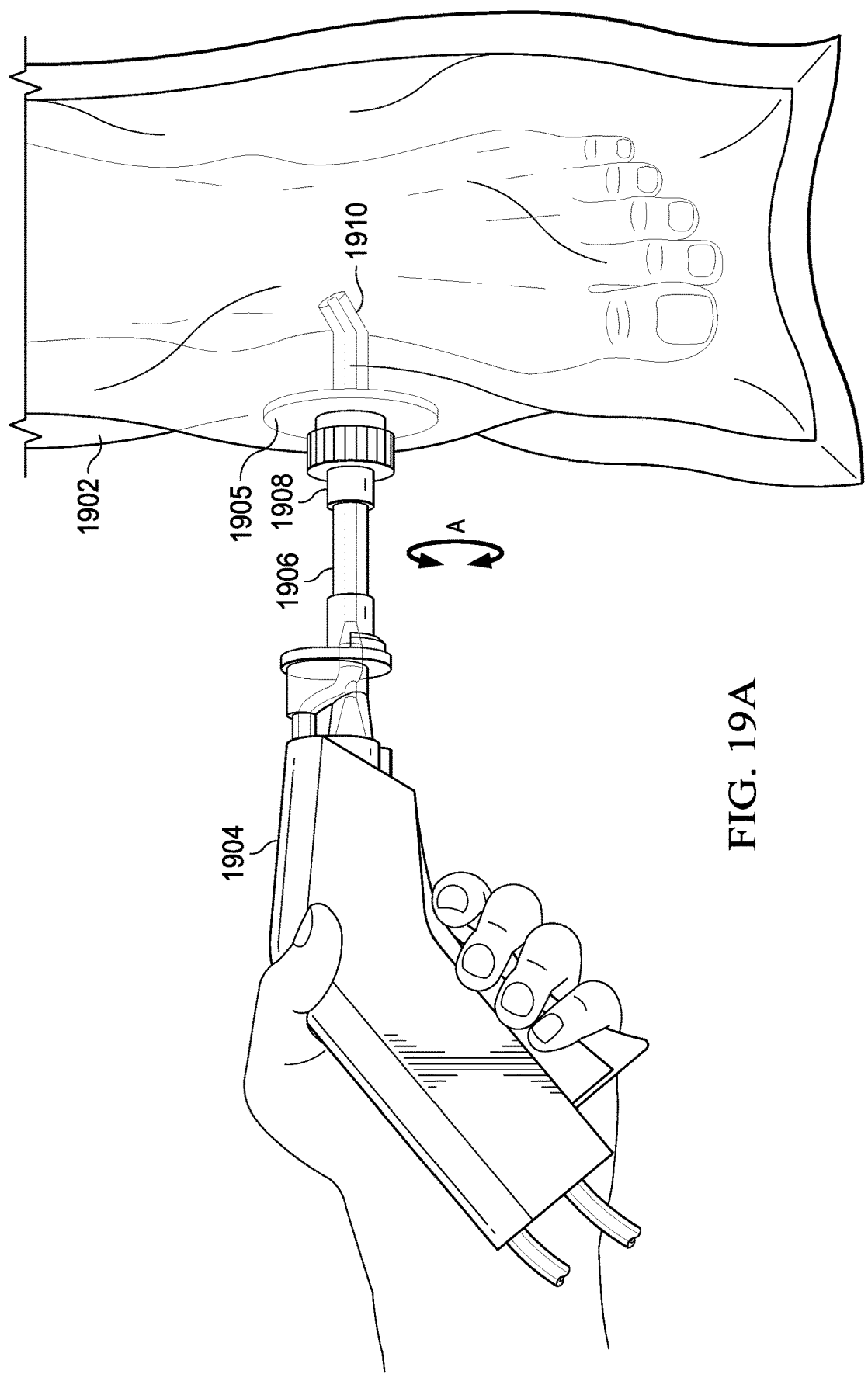
FIG. 19A is a perspective view of a lavage system used in conjunction with a preferred embodiment.
Figure 19B:
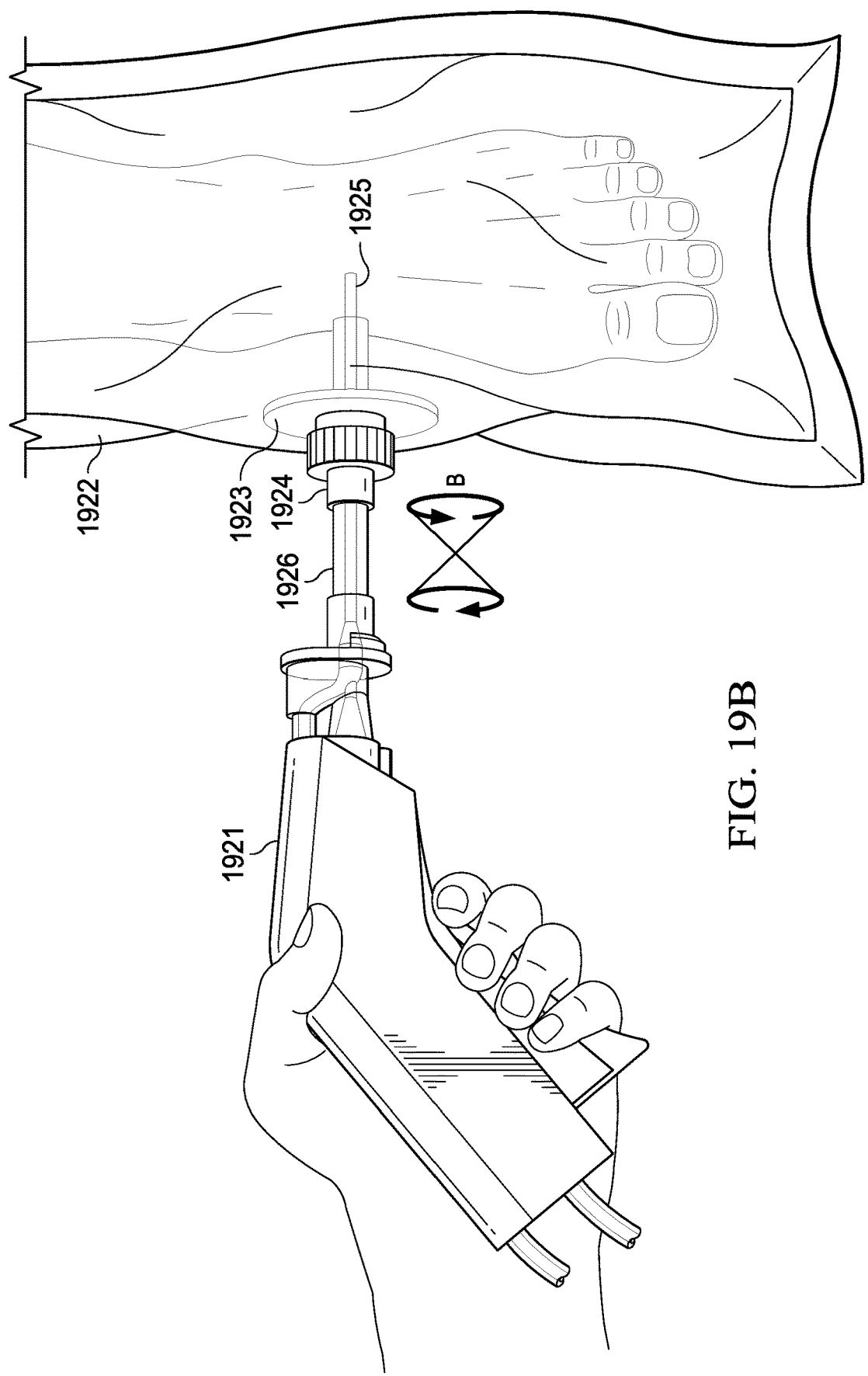
FIG. 19B is a perspective view of a lavage system used in conjunction with a preferred embodiment.

Referring then to FIG. 19A, a combination of an application bag as previously described with a lavage system is shown.

Application bag 1902 includes port connector 1905. The port connector is sealed to the exterior and in ducted communication with the interior of the application bag. Port connector 1905 includes rotary coupling 1908. Barrel 1906 is operatively disposed within rotary coupling 1908. Barrel 1906 includes angled tip 1910.

In use, lavage system 1904 is rotated about the axis of barrel 1906 in direction "A." In this way, the angled tip can be manipulated to direct high-pressure fluid to advantageous angles for wound treatment therapy without wrinkling or constricting the application bag.

Referring to 19B, an alternate embodiment of a combination of an application bag and a lavage system will be described.

Application bag 1922 includes port connector 1923. Port connector 1923 is sealed to the exterior of the application bag and is held in ducted communication with its interior. Port connector 1923 includes angled coupling 1924. Barrel 1926 of lavage system 1921 is connected to angled coupling 1924. Barrel 1926 extends through the angled coupling.

In use, as lavage system 1921 is rotated and translated, angled coupling 1924 allows lavage tip 1925 to be moved in the direction "B" as shown. The rotation and angular translation of the lavage tip allows for therapeutic use during wound treatment. Those in the art will recognize that moving the lavage system in 1921 as enabled to by the angled coupling allows varying angles to be used by lavage tip 1925 while preventing distortion, creasing and other undesirable effects between the application bag and the port connector.

Figure 20:
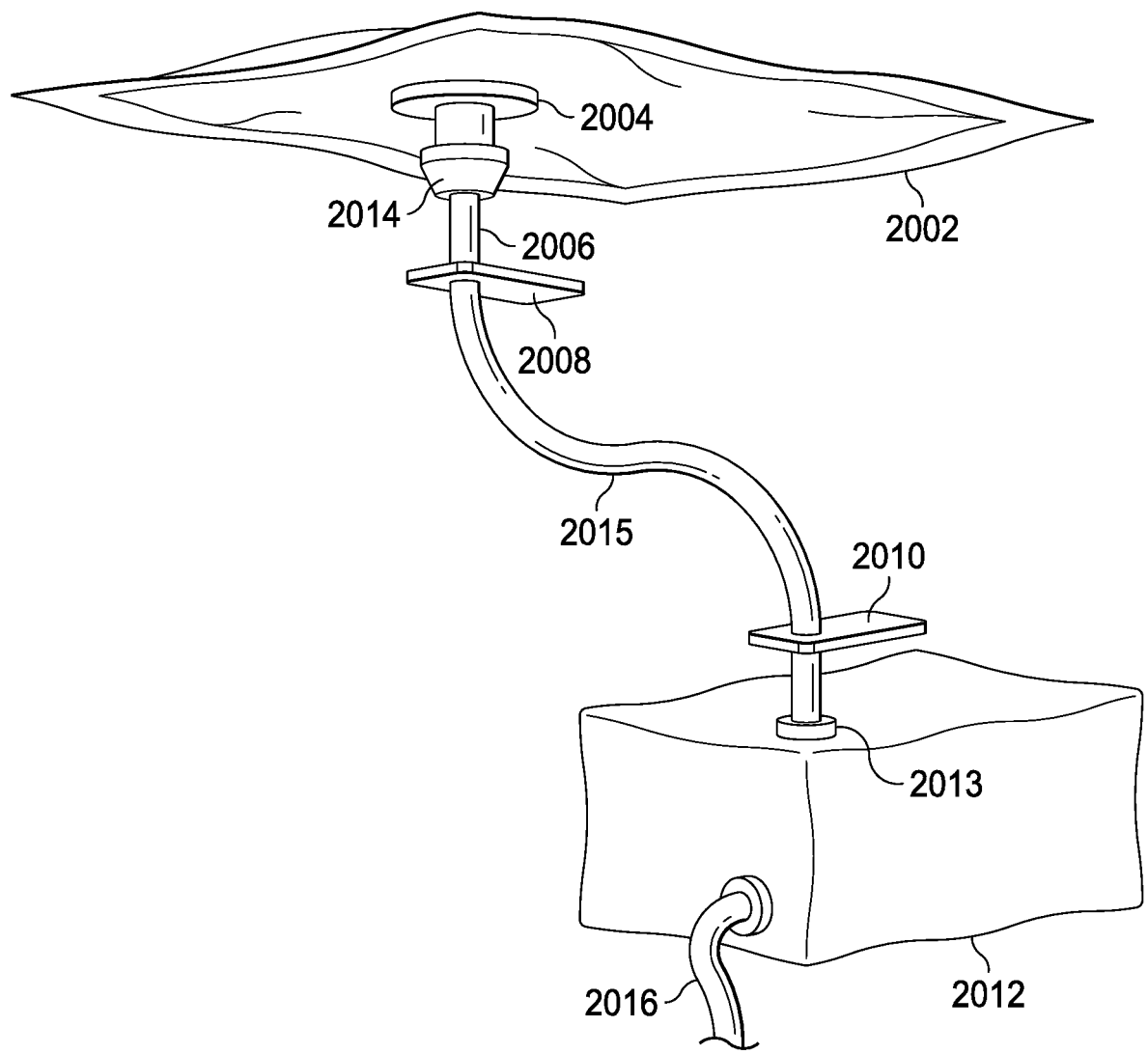
FIG. 20 is a perspective view of a draining system used in connection with a preferred embodiment.

Referring then to FIG. 20, use of the application bag in association with a collection bag will be described.

Application bag 2002 is fitted with port connector 2004. The port connector is sealed to the exterior and held in ducted communication with the interior of the application bag. Port connector 2004 is fitted to drain connector 2014. Drain connector 2014 is connected to drain tube 2006. Drain tube 2006 is further connected to collection bag 2012 through coupling 2013. Drain tube 2006 is fitted with clamp 2008 and clamp 2010. In between clamp 2008 and clamp 2010 is serrated cut line 2015.

In use, exhaust fluid from various procedures in the application bag are drained through the port connector and drain connector into the drain tube and on to collection bag 2012. In a preferred embodiment, gravity is used to move the exhaust fluid into the collection bag. In other embodiments, the collection bag may be fitted with a source of suction 2016. Once collection bag is full or if the procedure is ended, clamp 2008 and clamp 2010 may be advanced against drain tube 2006 to seal the connection between the port connector and the collection bag. Drain tube 2006 may then be bifurcated along serrated cut line 2015 with a cutting instrument. Collection bag 2012 may then be safely removed without the necessity of removing application bag 2002 from the patient.

Figure 21A:
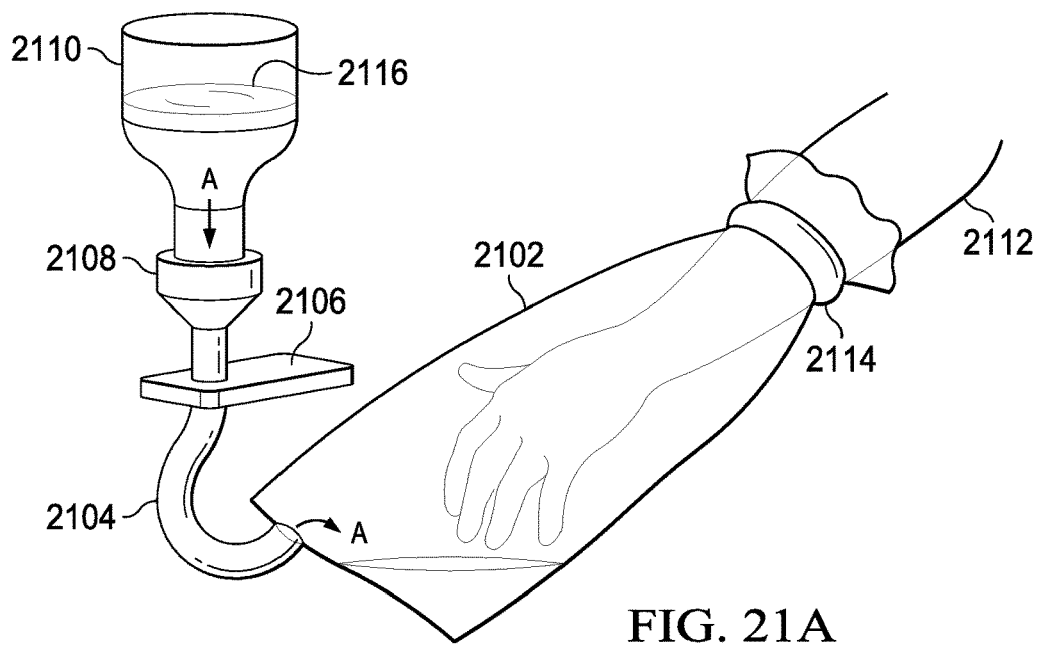
FIG. 21A is a perspective view of a draining system used in connection with a preferred embodiment.
Figure 21B:
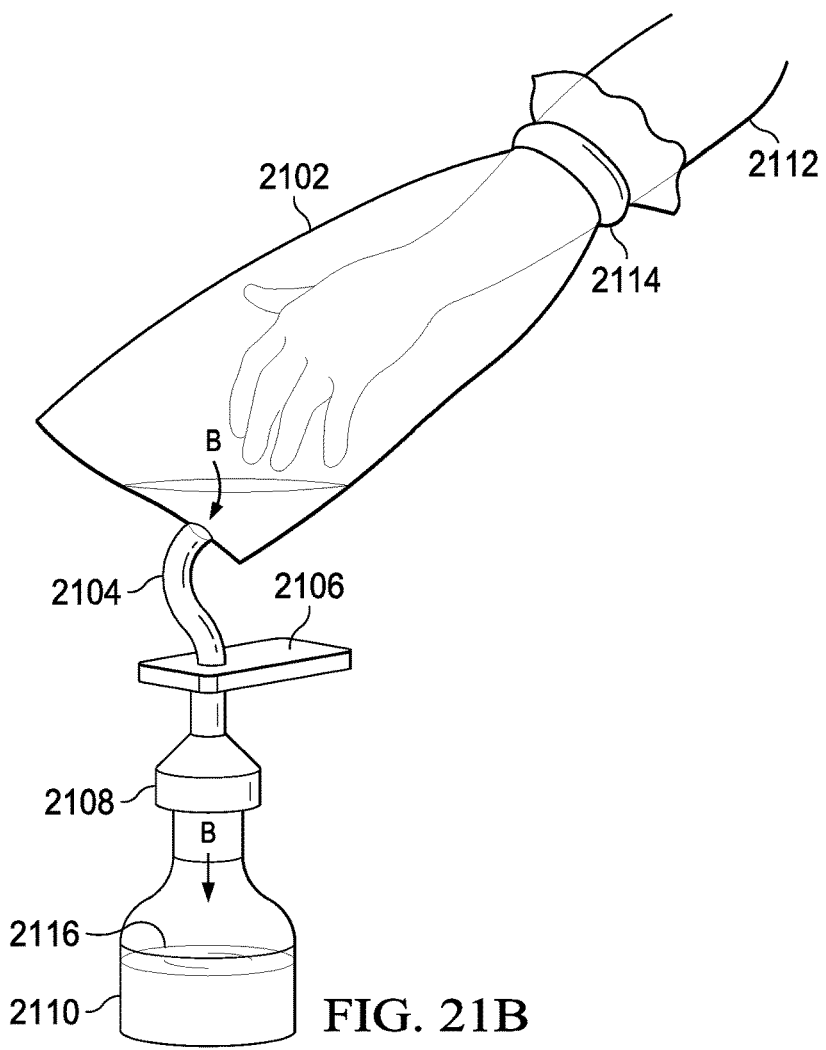
FIG. 21B is a perspective view of a draining system used in connection with a preferred embodiment.

Referring then to FIGS. 21A and 21B, a preferred embodiment of a draining system used in connection with a preferred embodiment will be described.

Application bag 2102 is applied to patient extremity 2112 with adhesive closure 2114, as previously described. Application bag 2102 is fitted with fill tube 2104 which proceeds to threaded cap 2108. Threaded cap 2108 is sealingly engaged with antiseptic bag 2110. Clamp 2106 is optimally disposed on fill tube 2104 to provide optional sealing of the fill tube when desired.

In FIG. 21A, antiseptic bag 2110 is positioned above patient extremity 2112 and application bag 2102. Antiseptic 2116 proceeds in direction "A" from the antiseptic bag through the fill tube and into the application bag where it is used to disinfect the patient extremity.

Referring then to FIG. 21B, after the patient extremity has been disinfected with the antiseptic, the application bag and the patient extremity is positioned above the antiseptic bag. The antiseptic drains in direction "B" from the application bag through fill tube 2104 and where upon it returns to antiseptic bag 2110.

During the filling and emptying processes described, clamp 2106 may be used the vary rate of flow of the antiseptic from or to the antiseptic bag. In this way, the antiseptic bag may be used to both deliver new antiseptic to the application bag and serve as a repository for exhausted antiseptic when the disinfecting procedure is completed.

The embodiments have been described in detail with particular reference to certain preferred embodiments thereof, but it will be understood that variations and modifications can be affected within the scope of the embodiments, especially to those skilled in the art.

The invention claimed is:

1. A device for applying an antiseptic preparation to an extremity of a patient comprising:
   a flexible container configured to surround the extremity;
   a split gasket, sealed to the flexible container, having a first adhesive surface;
   a first lateral seal section, having a second adhesive surface, sealed to the flexible container, adjacent the split gasket;
   a second lateral seal section, having a third adhesive surface, sealed to the flexible container, adjacent the split gasket and the first lateral seal section;
   an access hole, having a first perimeter, in the flexible container;
   a flap, having a second perimeter, adjacent the access hole;
   an adhesive layer between the first perimeter and the second perimeter; and,
   whereby, in a closed position, the flap covers the access hole and seals the first perimeter to the second perimeter;
   whereby, in an open position, the flap does not cover the access hole and does not seal the first perimeter to the second perimeter; and,
   whereby, in a closed configuration, the split gasket is sealed to the extremity by the first adhesive surface and the first lateral seal section is sealed to the second lateral seal section by connecting the second adhesive surface to the third adhesive surface.

2. The device of claim 1, wherein the split gasket is formed of an elastic material.

3. The device of claim 1, further comprising:
   a first removable protective sheet in contact with the first adhesive surface;
   a second removable protective sheet in contact with the second adhesive surface; and,
   a third removable protective sheet in contact with the third adhesive surface.

4. The device of claim 1, further comprising at least one access port ductedly connected to the flexible container.

5. The device of claim 1, further comprising a brush, removably fixed to an interior of the flexible container.

6. The device of claim 1, further comprising a drain port.

7. The device of claim 6, wherein the drain port further comprises a flexible nipple having a removable end.

8. The device of claim 1, further comprising:
   a drain line ductedly connected to the flexible container; and,
   a collection bag, ductedly connected to the drain line.

* * * * *